(12) United States Patent
Driesen et al.

(10) Patent No.: US 9,364,303 B2
(45) Date of Patent: Jun. 14, 2016

(54) CLEANING SECTION FOR AN ELECTRIC ORAL HYGIENE DEVICE

(75) Inventors: Georges Driesen, Weilrod (DE); Bernd Trebitz, Butzbach (DE); Eva Susanne Dominique Thurnay, Kronberg (DE); Heidrun Schmelcher, Oberursel (DE); Martin Haas, Frankfurt (DE); Thomas Fritsch, Eppstein (DE)

(73) Assignee: BRAUN GMBH, Kronberg (DE)

( * ) Notice: Subject to any disclaimer, the term of this patent is extended or adjusted under 35 U.S.C. 154(b) by 0 days.

(21) Appl. No.: 13/541,797

(22) Filed: Jul. 5, 2012

(65) Prior Publication Data

US 2013/0007969 A1      Jan. 10, 2013

(30) Foreign Application Priority Data

Jul. 6, 2011    (EP) ...................................... 11005504

(51) Int. Cl.
*A61C 17/34* (2006.01)
*A61C 17/22* (2006.01)
*A46B 9/02* (2006.01)

(52) U.S. Cl.
CPC .............. *A61C 17/3436* (2013.01); *A46B 9/025* (2013.01); *A46B 9/028* (2013.01); *A61C 17/222* (2013.01); *A46B 2200/1066* (2013.01)

(58) Field of Classification Search
CPC ........ A61C 17/34; A61C 17/22; A61C 17/26; A61C 17/3436; A46B 9/04
USPC .......................... 15/22.1, 22.2, 22.4, 28, 167.1
See application file for complete search history.

(56) References Cited

U.S. PATENT DOCUMENTS

| | | | | |
|---|---|---|---|---|
| 6,735,804 | B2 * | 5/2004 | Carlucci et al. | 15/28 |
| 6,826,797 | B1 * | 12/2004 | Chenvainu et al. | 15/110 |
| 7,389,557 | B2 * | 6/2008 | McDougall | 15/110 |
| 7,788,756 | B2 * | 9/2010 | Kraemer | 15/28 |
| 7,814,603 | B2 * | 10/2010 | Gavney, Jr. | 15/110 |
| 7,934,284 | B2 * | 5/2011 | Braun et al. | 15/22.1 |
| 7,941,886 | B2 * | 5/2011 | Chenvainu et al. | 15/22.4 |
| 8,141,192 | B2 * | 3/2012 | Gavney, Jr. | 15/22.1 |

(Continued)

FOREIGN PATENT DOCUMENTS

| | | |
|---|---|---|
| EP | 0 765 642 A2 | 4/1997 |
| JP | 09-168496 A | 6/1997 |

(Continued)

OTHER PUBLICATIONS

International Search Report for PCT/IB2012/053448 dated Sep. 17, 2012.

*Primary Examiner* — Michael Jennings
(74) *Attorney, Agent, or Firm* — Jay Anthony Krebs; James E. Oehlenschlager

(57) ABSTRACT

A cleaning section for an electric oral hygiene device is disclosed. The cleaning section includes at least a first carrier mounted for driven rotation or oscillating rotation around a rotation axis; and at least a plurality of first cleaning elements mounted on the first carrier with their bases arranged on the vertices of a first star-shaped polygon around the rotation axis. All of the first cleaning elements are inclined in a circumferential direction such that the free end of each of the first cleaning elements is farther away in the circumferential direction than the base of the respective first cleaning element; and wherein at least one cleaning element property alternates between adjacent first cleaning elements or between clusters of first cleaning elements.

5 Claims, 15 Drawing Sheets

(56) References Cited

U.S. PATENT DOCUMENTS

| | | |
|---|---|---|
| 8,185,993 B2 * | 5/2012 | Fischer et al. .................... 15/28 |
| 8,220,097 B2 * | 7/2012 | DePuydt et al. ............... 15/22.4 |
| 2001/0023516 A1 * | 9/2001 | Driesen et al. ............... 15/167.1 |
| 2002/0108194 A1 * | 8/2002 | Carlucci et al. .................... 15/28 |
| 2002/0138926 A1 * | 10/2002 | Brown et al. ................. 15/22.1 |
| 2002/0166188 A1 * | 11/2002 | Driesen et al. ................. 15/192 |
| 2011/0173765 A1 * | 7/2011 | Braun et al. ................... 15/22.1 |
| 2011/0296642 A1 * | 12/2011 | Driesen et al. ............... 15/167.1 |

FOREIGN PATENT DOCUMENTS

| | | |
|---|---|---|
| JP | 2004-000342 A | 1/2004 |
| WO | WO 02/45617 A1 | 6/2002 |
| WO | WO 02/067806 A1 | 9/2002 |
| WO | WO 03/073958 A1 | 9/2003 |

* cited by examiner

CLEANING SECTION FOR AN ELECTRIC ORAL HYGIENE DEVICE

CROSS REFERENCE TO RELATED APPLICATIONS

This application claims the benefit of European Patent Convention Application No. 11005504.3, filed Jul. 6, 2011, the substance of which is incorporated by reference in its entirety. herein.

FIELD OF THE INVENTION

The present disclosure is concerned with a cleaning section for an electric oral hygiene device and it is in particular concerned with such a cleaning section that has inclined cleaning elements.

BACKGROUND OF THE INVENTION

It is known that a cleaning section of an electric oral hygiene device can be equipped with a cleaning element mounted on a carrier of a cleaning head arranged for rotation or oscillatory rotation around a rotation axis, where the cleaning element is inclined against the rotation axis. In particular, the cleaning element may be inclined such that it crosses the rotation axis when viewed from the side. EP 0 765 642 A2 generally discusses a brush part of a toothbrush, which brush part has circumferentially inclined cleaning elements realized as bristle tufts.

One object for cleaning sections, in particular brush sections of an electric toothbrush, is to provide an arrangement of cleaning elements that provides good cleaning efficacy of hard to reach areas such as interproximal spaces, recessed areas of molars or surfaces of malpositioned teeth.

Thus it is a desire to provide a cleaning section for an electric oral hygiene device that provides an improved cleaning efficacy or at least a different cleaning behavior over the known cleaning elements.

SUMMARY OF THE INVENTION

In accordance with one aspect there is provided a cleaning section for an electric oral hygiene device that has at least a first carrier mounted for driven rotation or oscillating rotation around a rotation axis, at least a plurality of first cleaning elements mounted on the first carrier with their bases arranged on the vertices of a first star-shaped polygon around the rotation axis, wherein the bases lie on a mounting surface and the whole interior of the first star-shaped polygon is visible from the point where the rotation axis crosses the mounting surface, wherein all of the first cleaning elements are circumferentially inclined with respect to the rotation axis such that the free end of each of the first cleaning elements is farther away in the circumferential direction than the base of the respective first cleaning element and wherein the circumferential inclination direction of all first cleaning elements is the same, and wherein at least one cleaning element property of adjacent first cleaning elements or adjacent clusters of first cleaning elements discretely alternates between a first configuration and a second configuration.

In accordance with at least one aspect there is provided an electric oral hygiene device that has a cleaning section as proposed.

In accordance with another embodiment, a cleaning section for an electric oral hygiene is provided. The cleaning section includes, at least a first carrier mounted for driven rotation or oscillating rotation around a rotation axis; and at least a plurality of first cleaning elements mounted on the first carrier with their bases arranged on the vertices of a first star-shaped polygon around the rotation axis. All of the first cleaning elements are inclined in a circumferential direction such that the free end of each of the first cleaning elements is farther away in the circumferential direction than the base of the respective first cleaning element. At least one cleaning element property alternates between adjacent first cleaning elements or between clusters of first cleaning elements.

BRIEF DESCRIPTION OF THE DRAWINGS

Example embodiments of cleaning sections and of an electric oral hygiene device in accordance with at least one or more aspects of the present disclosure will be discussed in the following with reference to figures. In the figures

DETAILED DESCRIPTION OF THE INVENTION

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

Although the embodiments are described herein in the context of an electric oral hygiene device, such as an electric toothbrush, embodiments are not limited thereto. Embodiments disclosed herein may be implemented in a wide-variety of applications, such as in the application of an electric tongue cleaner, and many others.

Figure 1:
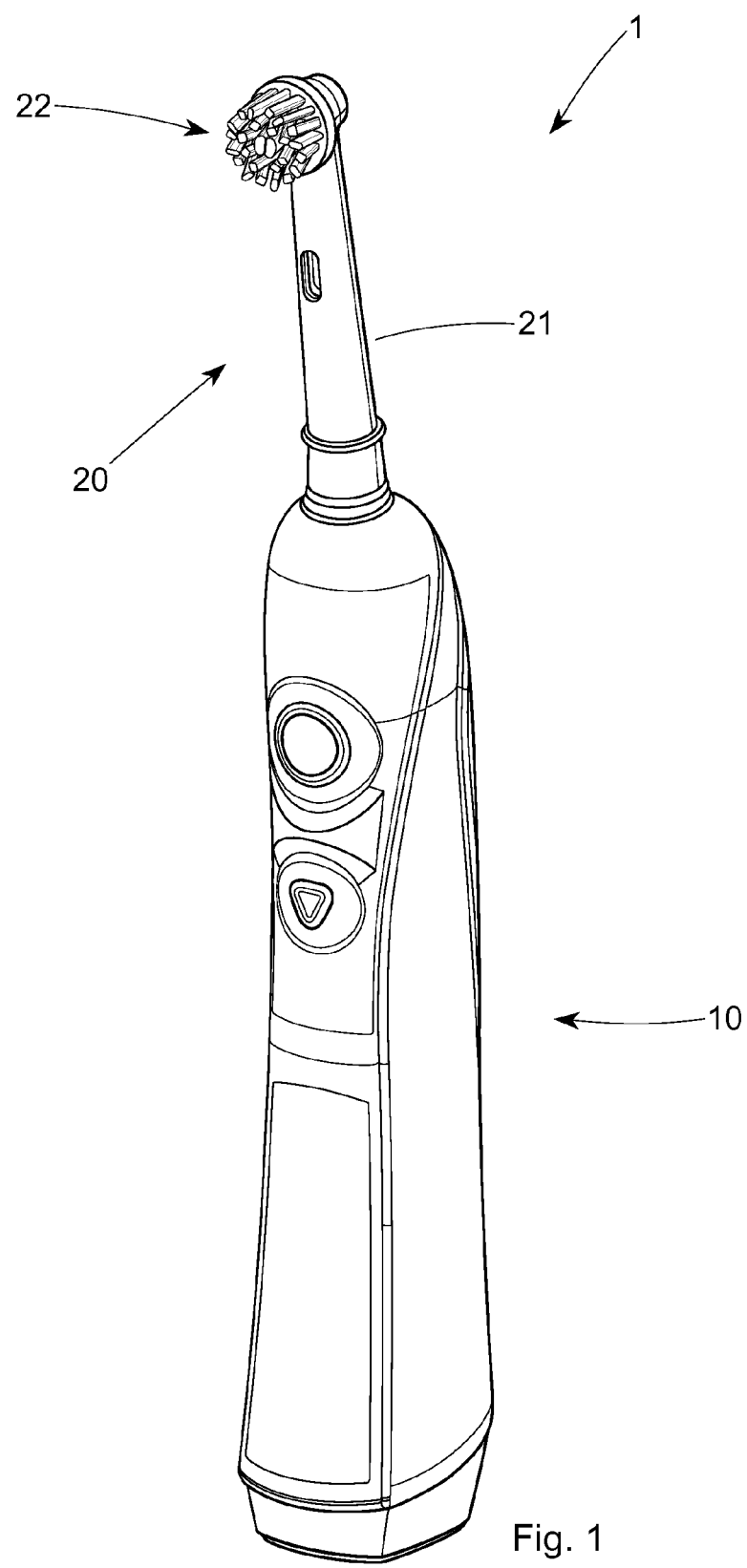
FIG. 1 is a perspective view onto an example embodiment of an electric oral hygiene device comprising a cleaning section in accordance with one or several aspects of the present disclosure.

FIG. 1 is a depiction of an example embodiment of an electric oral hygiene device 1 having a handle 10 and a cleaning section 20 that may be realized as a brush section, which cleaning section 20 may optionally be replaceable. The cleaning section 20 may comprise a housing 21 that may be elongated, optionally essentially tubular, and a movably arranged cleaning head 22 mounted at an end of the housing 21 distal to the handle. The cleaning head 22 may be realized as a brush head.

Figure 2:
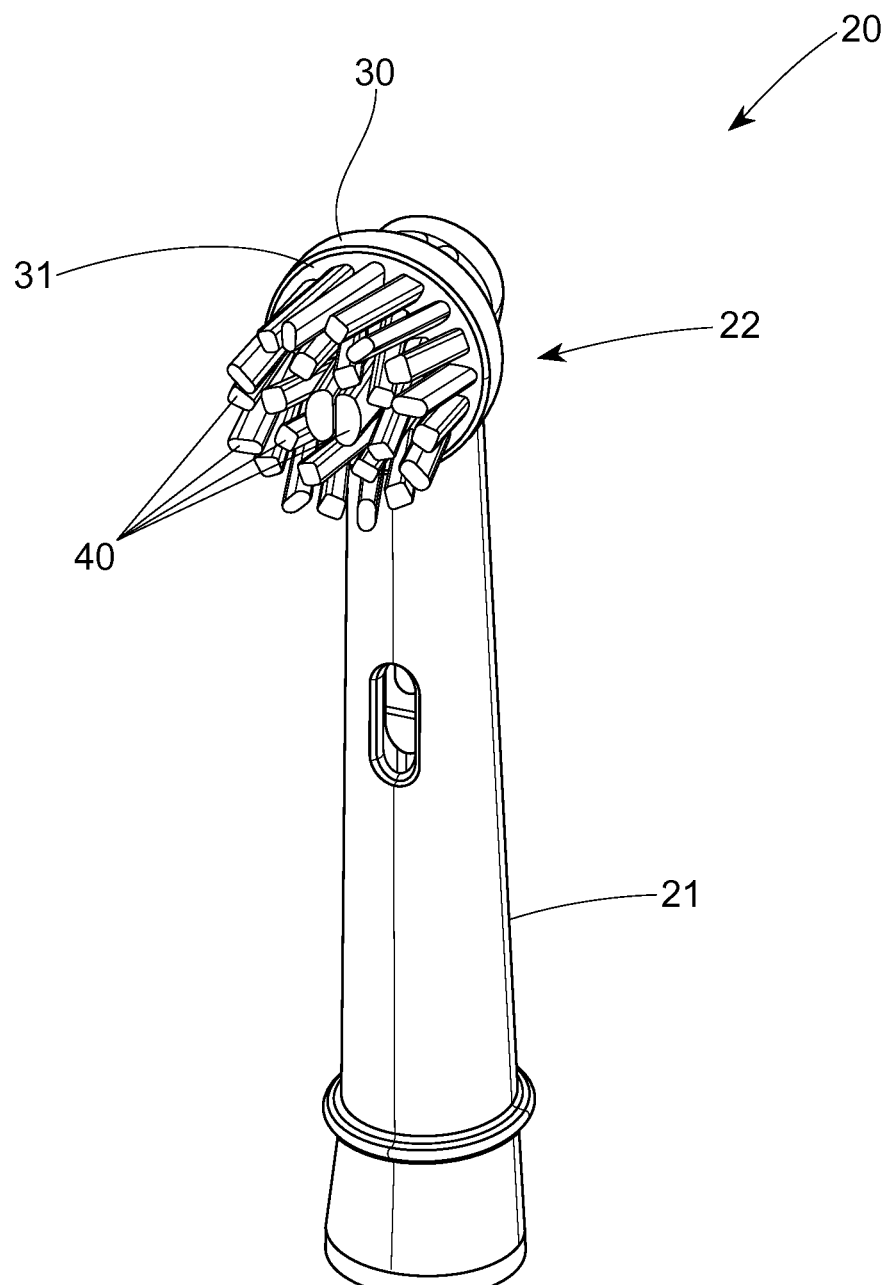
FIG. 2 is a perspective view onto an example embodiment of a cleaning section in accordance with one or several aspects of the present disclosure.

FIG. 2 is a depiction of an example embodiment of a cleaning section 20 that may be realized as a replaceable brush section. The cleaning section 20 comprises an elongated housing 21 that is suitable for insertion into the human oral cavity such that a cleaning head 22 (here realized as a brush head) enables cleaning of hard to reach areas such as the surfaces of the molars or the wisdom teeth, surfaces of malpositioned teeth, recessed areas, interproximal spaces etc. The cleaning head 22 comprises a first carrier 30 having a mounting surface 31 on which cleaning elements 40 are mounted. The cleaning head 22 is mounted such that it can in operation be driven into a rotation or oscillating rotation around a rotation axis when the cleaning section 20 is attached to a handle of an electric oral cleaning device. At least some of the cleaning elements 40 are inclined with respect to the mounting surface 31, which will be explained in more detail in the following.

Figure 3:
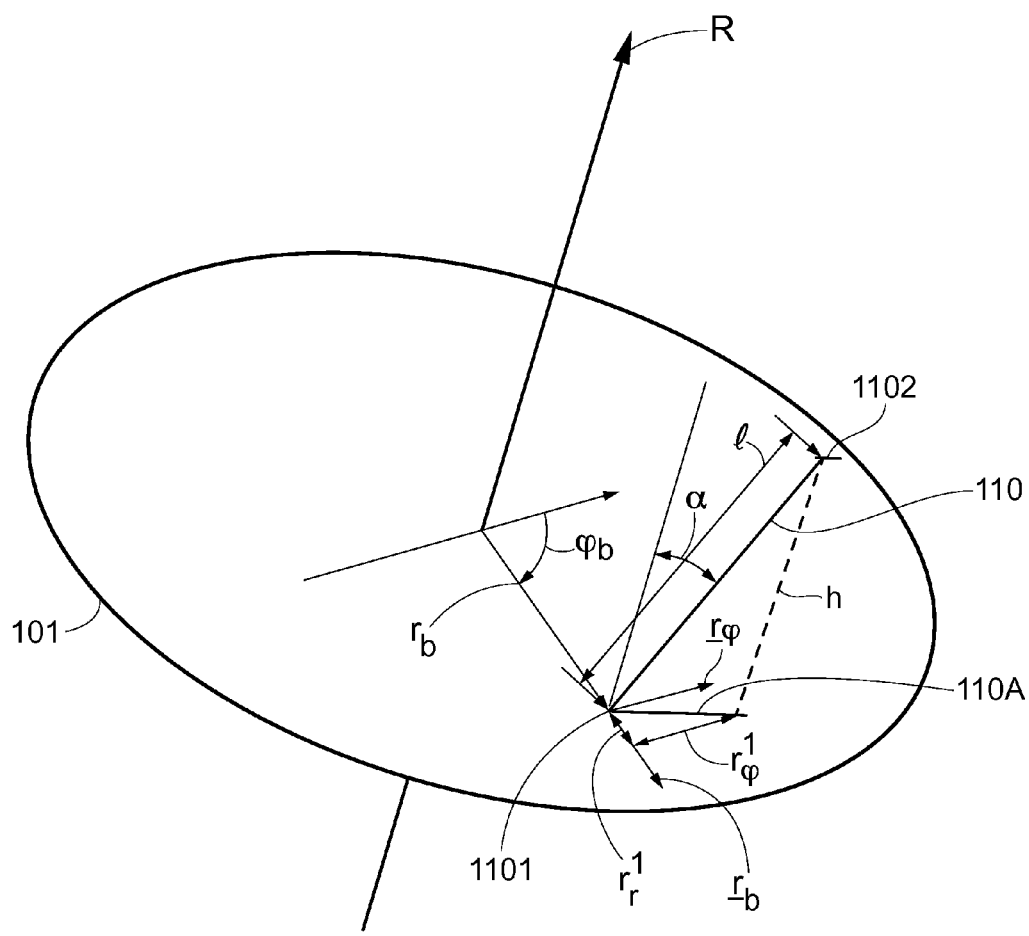
FIG. 3 is a schematic depiction of a mounting surface of a carrier on which a schematic cleaning element is mounted and in which geometrical parameters are indicated.

FIG. 3 is a schematic depiction of an example cleaning element 110 (for sake of simplicity here reduced to a line—which may be seen as the centre line of an extended cleaning element) mounted on a schematically shown flat mounting surface 101 of a carrier. It shall be assumed that the carrier is mounted for rotation (or oscillating rotation) around a rotation axis R that is perpendicular to the flat mounting surface 101. While the mounting surface is here shown as a plane, this shall not limit the mounting surface within the present disclosure to flat surfaces. Curved surfaces such as portions of a cylinder surface or of a spherical surface may also be considered. The base 1101 of the cleaning element 110 has a location on the mounting surface 101 that can be defined with respect to the location where the rotation axis R crosses the mounting surface 101 by means of polar coordinates $r$ and $\phi$ (radial distance and relative angular position with respect to a radial reference beam). The base 1101 of the cleaning element 110 has a location on the mounting surface 101 that is given by $r_b$ and $\phi_b$. The cleaning element 110 has a free end 1102 and a length l. The parallel projection 110A of the cleaning element 110 along the direction of the rotation axis R onto the mounting surface 101 can be divided into a portion $r_r^\perp$ that extends along the radial beam $\underline{r}_b$ originating at the rotation axis and going through the base 1101 of the cleaning element 110 and into a portion $r_\phi^\perp$ that extends into a circumferential direction $\underline{r}_\phi$ that lies in the plane defined by the mounting surface 101, that is perpendicular to the radial beam $\underline{r}_b$ and that crosses the base 1101 of the cleaning element 110. A cleaning element being inclined such that it has a finite radial portion $r_r^\perp$ of its parallel projection but where the circumferential portion $r_\phi^\perp$ is zero, $r_\phi^\perp=0$, is not inclined in circumferential direction but is only inclined in radial direction. Hence, a cleaning element that is circumferentially inclined has a non-zero circumferential portion $r_\phi^\perp$ of its parallel projection and may also have a non-zero radial portion $r_r^\perp$. A cleaning element where also the radial portion $r_r^\perp$ is zero, $r_r^\perp=0$, is not inclined with respect to the rotation axis but extends parallel to the rotation axis. Circumferential inclination can occur either in clockwise direction or in counter-clockwise direction. Thus, when reference is made to the "same" circumferential inclination direction with respect to two or more cleaning elements, it is meant that these two or more cleaning elements are all circumferentially inclined in either clockwise direction or all in anti-clockwise direction. In case that the parallel projection 110A of the cleaning element 110 has a zero radial portion ($r_r^\perp=0$) and a non-zero circumferential portion ($r_\phi^\perp\neq0$), then the cleaning element 110 is only circumferentially inclined within the meaning of the present disclosure. In such a case, the parallel projection 110A extends along a tangent at a circle around the rotation axis having a radius $r_b$, where the base of the cleaning element forms the touch point at the circle. In the shown example, the free end 1102 of the cleaning element 110 lies radially farther outward than the base 1101. This situation would still exist in cases where the cleaning element 110 has zero radial inclination (i.e. where the cleaning element is only circumferentially inclined) in accordance with the here given definition of radial inclination. An (total) inclination angle $\alpha$ of the cleaning element 110 relative to the rotation axis R is defined as the angle between a line parallel to the rotation axis that extends through the base 1101 of the cleaning element 110 and the centre line of the cleaning element 110. In case that the inclination angle $\alpha$ is zero, $\alpha=0$, the height h of the cleaning element measured in the direction of the rotation axis is identical to the length l of the cleaning element 110. In case the cleaning element 110 is inclined by an angle $\alpha$ relative to the rotation axis R, then the height h is less than the length l, $h=l\cdot\cos(\alpha)<l$.

The present disclosure is generally concerned with a cleaning section that has at least a plurality (i.e. more than two, but—as will be discussed—plurality in the present disclosure mentioned with respect to the first cleaning elements may imply that there are at least four first cleaning elements) of first cleaning elements mounted on a mounting surface of a first carrier, where the bases of the first cleaning elements are arranged on the vertices of a star-shaped polygon and where all the first cleaning elements are circumferentially inclined in the same circumferential direction (i.e. where all the first cleaning elements have a non-zero circumferential portion $r_\phi^1$ in the same circumferential direction, i.e. the first cleaning elements are either all circumferentially inclined in clockwise direction or in anti-clockwise direction, and optionally each cleaning element may also have a non-zero radial portion $r_r^1$). The first carrier is arranged for driven rotation or oscillating rotation around a rotation axis.

The present disclosure is in one aspect concerned with such a cleaning section as mentioned, where at least a cleaning element property of the first cleaning elements discretely alternates between adjoining (or: adjacent) first cleaning elements or between adjoining clusters of first cleaning elements such that for every given first cleaning element the cleaning element property has a first configuration while for the two neighboring first cleaning elements lying on the two neighbor vertices of the first star-shaped polygon the respective cleaning element property has a second configuration. In other words, when adjoining first cleaning elements are considered, for every second first cleaning element the cleaning element property has the first configuration and for the other cleaning elements the cleaning element property has the second configuration. The concept of adjoining clusters of first cleaning elements is explained in more detail with reference to FIG. 8 (fifth example embodiment) further below.

For the purposes of the present disclosure, a "polygon" is a figure lying in a two-dimensional (in particular flat) plane (which plane may in particular coincide with a mounting surface of the carrier), which figure is bounded by a closed path, composed of a finite sequence of straight line segments (i.e., by a closed polygonal chain). These segments are called the edges of the polygon, and the points where two edges meet are the vertices of the polygon. A "star-shaped polygon" is a polygon where the whole interior is visible from at least one single point inside of the figure (in accordance with the present disclosure, the point where the rotation axis crosses the mounting surface of the carrier is such a point), i.e. where any straight line from this single point to any point on the edges of the polygon does not cross any other edge of the polygon (see in particular: Franco P. Preparata, Michael Ian Shamos: *Computational Geometry: An Introduction*, *Springer* Verlag, 1985, e.g. page 18). Such a star-shaped polygon is "simple" (i.e. the edges do not cross themselves) and may be "convex" (i.e. all points inside of the figure are points fulfilling the condition that the whole interior is visible from this point) or "concave" (i.e. at least one point exists inside of the figure from which the whole interior is not visible). As will be explained in more detail further below, the vertices of the star-shaped polygon may lie on a smooth curve and in particular on a differentiable and closed curve such as the edge of a circle, an ellipse or an oval or the vertices may at least be close to such a curve. In particular, the vertices of the polygon may lie within a band that has a radial width that is 25% or less of the radial distance between the respective band centre and the point where the rotation axis crosses the mounting surface. The band width may in particular be 20% or less, 15% or less, 10% or less, 5% or less, 4% or less, 3% or less, 2% or less, or 1% or less.

The term "cleaning element" (whether it refers to a first cleaning element or any other cleaning element) is used to refer to any suitable element which can be inserted into the oral cavity. Some suitable elements include bristle tufts, elastomeric massage elements, elastomeric cleaning elements, massage elements, tongue cleaners, soft tissue cleaners, hard surface cleaners, combinations thereof, and the like. The cleaning elements may include a wide variety of materials and may have a number of different configurations. Any suitable material and/or any suitable configuration may be utilized. For example, in some embodiments, the cleaning elements may comprise tufts. The tufts may comprise a plurality of individual filaments which are securely attached to a cleaning element carrier. Such filaments may be polymeric and may include polyamide or polyester or a thermoplastic elastomeric polyamide grind or mixtures thereof. In general, materials that may be used for manufacturing a cleaning element include thermoplastic elastomer (TPE), polyamide (PA), polybutylene terephthalate (PBT) and polyester (PES) in general, polypropylene (PP), polyethylene (PE) etc. The longitudinal and cross sectional dimensions of the filaments and the profile of the filament ends can vary. Additionally, the stiffness, resiliency and shape of the filament end can vary. Some examples of suitable dimensions include a length between about 6.0 mm and about 10 mm and in another embodiment between about 7.0 mm and about 8.5 mm, or any individual number within these ranges. Additionally, the filaments may include a substantially uniform cross-sectional dimension of between about 100 to about 350 microns, in another embodiment in a range of between about 125 microns and about 175 microns, or any individual number within these ranges. The tips of the filaments may be any suitable shape, examples of which include a smooth tip, a rounded tip, tapered and a pointed tip. In some embodiments, the filaments may include a dye which indicates wear of the filaments as described in U.S. Pat. No. 4,802,255. Other suitable examples of filaments are described in U.S. Pat. No. 6,018,840. In some embodiments, the cleaning element fields may comprise fins as described in U.S. Pat. No. 6,553,604, and U.S. Patent Application Publication Nos. 2004/0177462; 2005/0235439; and 2005/0060822. In some embodiments, the cleaning element fields may comprise a combination of fins and tufts.

A cleaning element property in accordance with the present disclosure may be the length of the cleaning element between base and free end, the area of the cross-section or the shape of the cross-section of the cleaning element (the cross section being taken either in a plane perpendicular to the rotation axis or in a plane perpendicular to the longitudinal extension axis of the cleaning element), the radial inclination angle, the circumferential inclination angle, the (total) inclination angle, the surface structuring of the cleaning element, the material the cleaning element is made of, or the cleaning element composition. Where the cleaning element is realized as a bristle tuft, the cleaning element composition refers e.g. to the bristle composition of the bristle tuft. Number of bristles, cross-sectional area or cross-sectional shape of each of the bristles of a bristle tuft, bristle material or bristle materials of each of the bristles, bristle structuring of each of the bristles, bristle stiffness or resilience of each of the bristles, etc. determine then the cleaning element composition. In accordance with the present disclosure, the cleaning element property discretely alternates between two configurations when the succession of cleaning elements arranged on the vertices of a star-shaped polygon is considered. With a configuration a value may be meant, e.g. in case that the cleaning element property is the length of the cleaning elements or the area of the cross section. configuration also may mean e.g. the composition of the cleaning element, where the cleaning element property discretely alternates between two compositions. With the term "discretely alternates" it shall be made particularly clear that each cleaning element has only one of two possible configurations of the alternating cleaning element property.

Cleaning elements such as bristles arranged on a carrier intended for (oscillatory) rotational movement that are circumferentially inclined may be bent into a more straight position relative to the mounting surface during operation in case that the movement direction of the cleaning element over a surface (such as the tooth surface) coincides with the inclination direction. This is caused by e.g. friction between the cleaning element tip and the surface (e.g. tooth surface) and/or by the cleaning element tip entering into a depression, i.e. into interproximal areas or recessed structures of a molar and becoming caught in the depression. When the cleaning element is bent into a more straight position, the cleaning element extends higher with respect to the mounting surface than in the inclined position. Hence, cleaning element entering depressions or recessed areas will penetrate into the depression and will thereby loosen debris and plaque potentially in a more effective manner than straight bristles that will not be able to perform additional penetration motion. This effect is likely to be enhanced in case that the penetration action is periodically changing. Hence, in case of cleaning element arranged as bristle tufts mounted on a bristle carrier at the vertices of a polygon around the rotation axis, interproximal cleaning is enhanced if all tufts are circumferentially inclined in the same direction in contrast to straight bristle tufts. Interproximal cleaning is likely to be further enhanced in case that the inclined bristle tufts have a discretely alternating cleaning element property such as an alternating cleaning element length, alternating cleaning element cross section, or alternating cleaning element composition etc. as the alternate arrangement leads to an alternating cleaning action that may in an improved way loosen and remove the debris and plaque.

In case that the (total) inclination angle lies in the range of between about 10 degrees to about 16 degrees, the additional penetration amplitude may lie in a relative range of between about 1.5% and 3.9% of the length of the cleaning element, hence in case a cleaning element length of 8.5 mm is assumed, the penetration amplitude has an additional amplitude in a range of between about 0.13 mm to about 0.33 mm, which is similar to the poking motion amplitude realized by e.g. electric toothbrushes that have a poking motion in addition to a scrubbing motion or e.g. cleaning oscillatory/rotational motion such as the Oral-B™ Triumph 5000.

Starting at a vertex v1, the succession of vertices of a star-shaped polygon having n vertices, when going along the edges of the polygon in a first direction, is v1, v2, v3, . . . , vn−1, vn. In accordance with the present disclosure, a cleaning element that is arranged with its base at vertex v1 is adjacent the cleaning elements that have their bases arranged on the vertices v2 and vn. Similarly, a cleaning element that is arranged with its base at vertex v2 is adjacent the cleaning elements that have their bases arranged on the vertices v1 and v3.

In the following, several example embodiments of cleaning heads of cleaning sections are described. While these example embodiments show certain combinations of features of possible cleaning heads in accordance with at least an aspect of the present disclosure, it is noted that this shall not mean that these features are to be seen as necessarily connected but that all features described herein are to be considered as individual features that can be combined in all possible variations as long as those variations are not contradictory to the gist and scope of the present disclosure.

First Example Embodiment

Figure 4A:
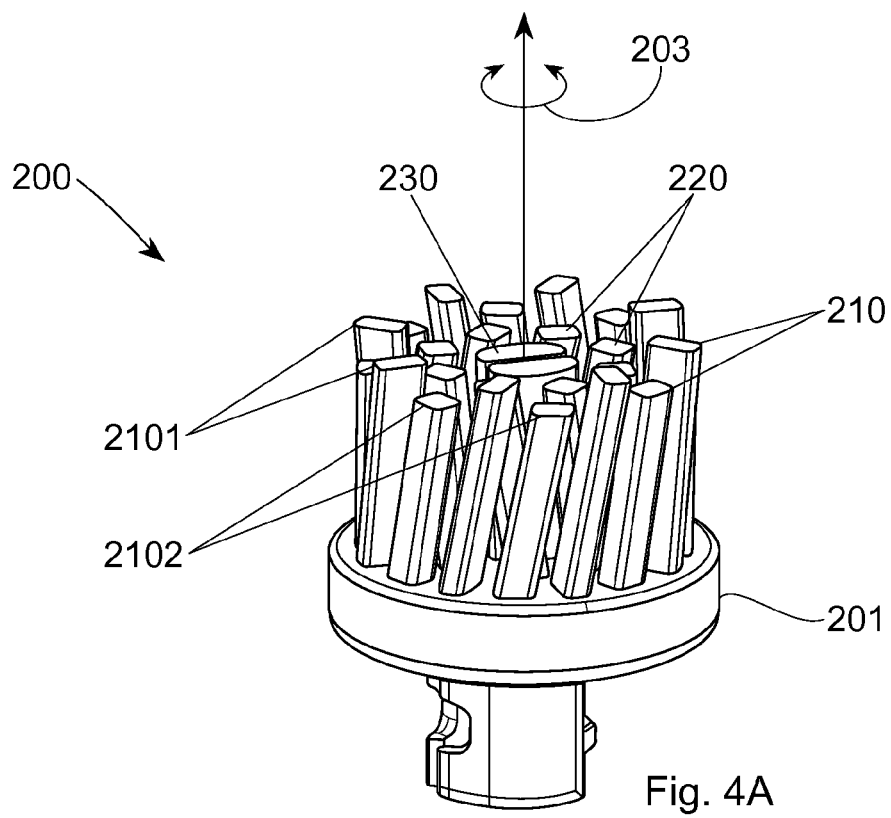
FIG. 4A is a perspective depiction of a first example embodiment of a cleaning head of a cleaning section in accordance with the present disclosure.
Figure 4B:
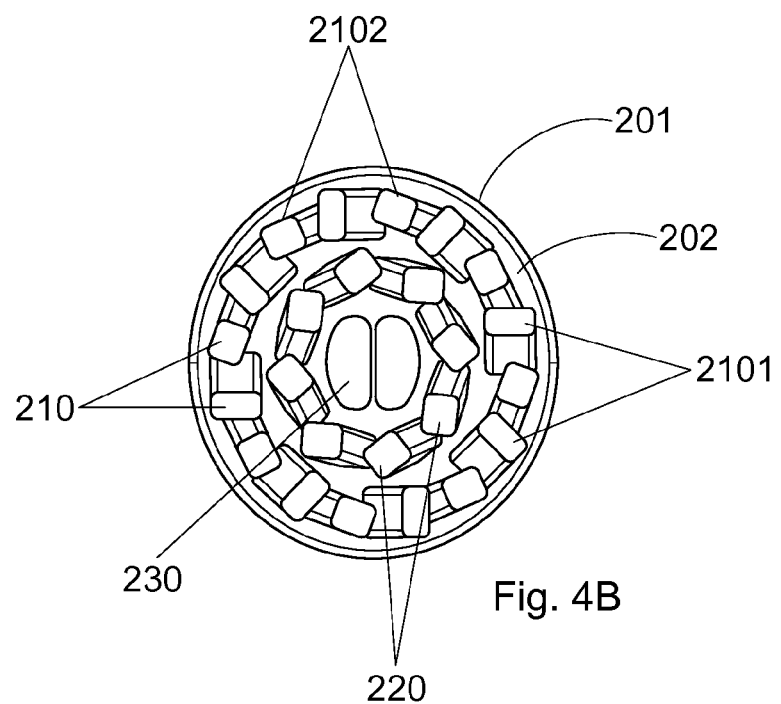
FIG. 4B is a top view onto the cleaning head shown in FIG. 4A.
Figure 4C:
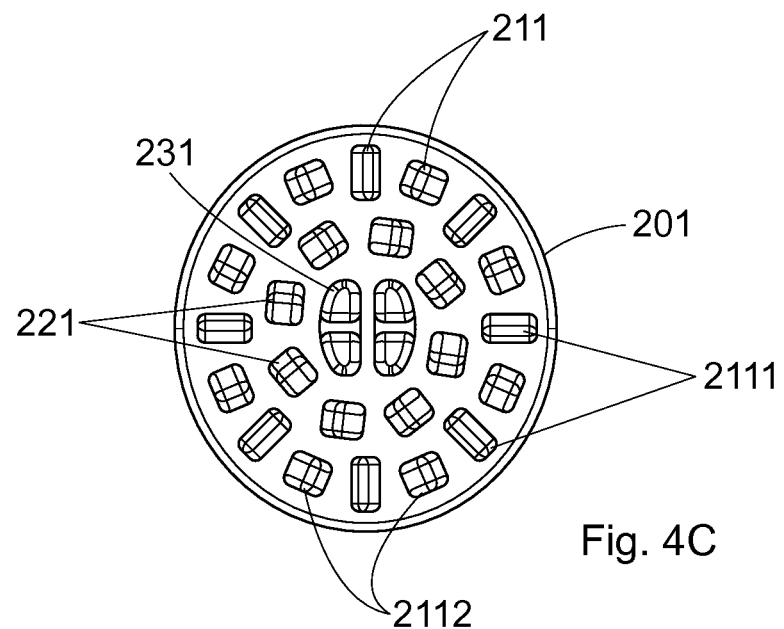
FIG. 4C is a top view onto a carrier used in the cleaning head shown in FIG. 4A without mounted cleaning elements.
Figure 4D:
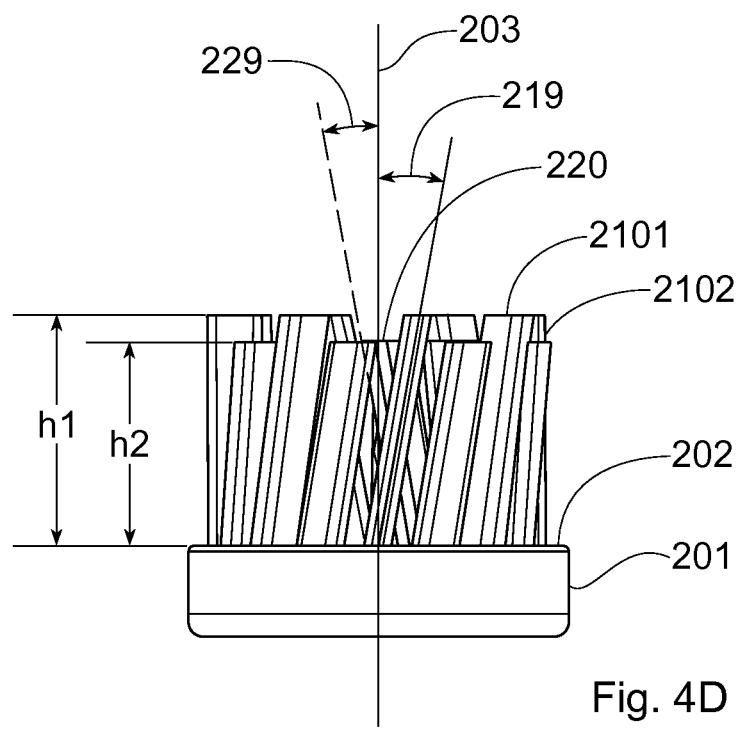
FIG. 4D is a side view onto the cleaning head shown in FIG. 4A.

FIG. 4A is a perspective view onto a first example embodiment of a cleaning head 200 of a cleaning section in accordance with an aspect of the present disclosure, FIG. 4B is a top view onto the cleaning head 200 shown in FIG. 4A, FIG. 4C is a top view onto the carrier 201 of the cleaning head 200 shown in FIG. 4A, and FIG. 4D is a side view onto the cleaning head shown in FIG. 4A.

From FIG. 4A and FIG. 4B it can be seen that the example cleaning head 200 comprises a cleaning element field having two ring-like arrangements of first cleaning elements 210 and second cleaning elements 220 that are mounted on a first carrier 201 and further elongated, kidney-shaped third cleaning elements 230 that are arranged in the centre of the cleaning element field. While the first cleaning elements 210 here seem to resemble a ring-like arrangement, their bases are generally arranged on the vertices of a star-shaped polygon around the rotation axis 203, which vertices may thus not necessarily lie on a differentiable and convex curve around the rotation axis, such as the edge of a circle, oval, or ellipse. The outer ring of first cleaning elements 210 may comprise sixteen cleaning elements that may be circumferentially inclined in counter-clockwise direction. Generally, the number of first cleaning elements (or second cleaning elements, if such are present in an embodiment) can be freely chosen (but in order to lie on the vertices of a star-shaped polygon, three or more first cleaning elements should be present). The inner ring-like arrangement comprises eight second cleaning elements 220 that may be circumferentially inclined in clockwise direction (i.e. in a circumferential inclination direction opposed to the circumferential inclination direction of the first cleaning elements). Two third cleaning elements 230 are arranged in the centre of the two rings, which third cleaning elements 230 may be straight (i.e. extend parallel to the rotation axis 203) and may be elongated and roughly kidney-shaped. The outer ring of first cleaning elements 210 comprises two sub-groups of first cleaning elements that are alternately arranged (where alternately arranged is meant with respect to the succession of vertices of the first star-shaped polygon). In the shown example, the two sub-groups 2101 and 2102 of first cleaning elements differ at least in two cleaning element properties: length (measured from base to tip) and shape of the cross-section (where the cross section may be taken in a plane perpendicular to the rotation axis 203). The first alternating cleaning element property is thus the length that discretely alternates between a first configuration (i.e. a first length value) and a second configuration (i.e. a second length value). The second alternating cleaning element property is the shape of the cross section that discretely alternates between a first configuration (i.e. a first shape) and a second configuration (i.e. a second shape).

Generally and applicable to all possible embodiments in accordance with at least one aspect of the present disclosure, the first cleaning elements may comprise two sub-groups of cleaning elements that are alternately arranged, where the cleaning elements of the two sub-groups differ in at least one cleaning element property, wherein for the first sub-group the cleaning element property takes a first configuration and for the second sub-group the cleaning element property takes a second configuration. Generally and applicable to all embodiments of the present disclosure, the presence of one discretely alternating cleaning element property of adjacent cleaning elements shall neither exclude the presence of one or more other cleaning element properties that may change from one to the other cleaning element in an arbitrary manner nor that one or more other cleaning element properties may also discretely alternate between adjacent cleaning elements.

The first and second cleaning elements 210 and 220 may have an (total) inclination angle of 10 to 16 degrees, while in general a (total) inclination angle within the range of about 2 degrees to about 35 degrees including all values lying there between is considered. It is to be noted that the inclination angle of the first cleaning elements may generally be chosen to lie in a range of between about 2 degrees and about 35 degrees, optionally in a range of between about 5 degrees to about 25 degrees and further optionally in a range of between about 8 degrees to about 20 degrees. Optionally, the inclination angle of the first cleaning elements may—additionally or alternatively to other alternating cleaning element properties of the first cleaning elements—discretely alternate between two inclination angle values, e.g. between 15 degrees and 17 degrees or between 10 degrees and 13 degrees etc. Optionally, only the radial or circumferential inclination angle may discretely alternate while the (total) inclination angle of the first cleaning elements itself is constant.

Generally and applicable in all embodiments where second cleaning elements are present, an inclination angle of the second cleaning elements may be chosen rather freely—the second cleaning elements may in some embodiments even have no inclination angle. Optionally the second cleaning elements may have an inclination angle that is equal to or less than the inclination angle of the first cleaning elements. In case that the second cleaning elements are arranged inwards of the first cleaning elements, a lower inclination angle than the inclination angle of the first cleaning elements is likely to stabilize the centre of the cleaning field in operation under pressure, i.e. when the cleaning elements are pushed against a tooth surface.

In the first example embodiment visualized by FIGS. 4A-4D, the first sub-group of first cleaning elements 2101 has a larger length (and thus also a larger height) than the second sub-group of first cleaning elements 2102. Further, the cleaning elements of the first sub-group 2101 of first cleaning elements have an elongated, roughly rectangular cross section (which can be more clearly seen in FIG. 4B), where the longer axis of the elongated cross section is essentially radially oriented, while the second sub-group 2102 of first cleaning elements have a more compact, roughly square cross section, where a slightly longer axis may be essentially circumferentially oriented. The second cleaning elements 220 all have essentially the same cross-sectional shape, which may be similar or identical to the almost square cross section of the second sub-group of first cleaning elements. Here, the cross section of the second cleaning elements 220 is similar or almost identical to the cross section of the first cleaning elements 2102 of the second sub-group. The height of the second cleaning elements 220 and of the third cleaning elements 230 is identical to the height of the second sub-group 2102 of first cleaning elements. The free ends of the first, second and third cleaning elements 210, 220, and 230 are cut flat and parallel to the flat mounting surface of the first carrier 201.

Generally and applicable in all possible embodiments, the first, second or third cleaning elements may be realized as bristle tufts, but this shall not exclude that some of the first, second or third cleaning elements are differently realized, e.g. as elastomeric elements.

While the first example embodiment shows one possible realization of a cleaning head of a cleaning section in accordance with one aspect of the present disclosure, it is generally to be noted that other embodiments may only comprise first cleaning elements having their bases arranged on the vertices of a first star-shaped polygon. Further cleaning elements may or may not be present. E.g. one or more further cleaning elements may be arranged farther away from the rotation axis than the first cleaning elements and alternatively or additionally one or more further cleaning elements may be arranged more proximate to the rotation axis than the first cleaning elements. As in accordance with one aspect of the present disclosure, the first cleaning elements are all circumferentially inclined in the same circumferential direction, the first cleaning elements may have any alternating cleaning element property such as alternating length or alternating (radial, circumferential or total) inclination angle or alternating cross-sectional shape or cross-sectional area etc. The first cleaning elements may have optionally two or even more cleaning element properties that may alternate or that may change between adjoining cleaning elements, e.g. they may have alternating length and alternating (radial) inclination angle or they may have alternating cleaning element composition while the length may vary (e.g. to form a cylindrical depression as is discussed with reference to the second example embodiment). The first cleaning elements may alternately be realized as elastomeric elements and bristle tufts. The first cleaning elements may all be circumferentially inclined in clockwise direction or all in counterclockwise direction.

FIG. 4B in particular shows the "double helix"-like structure of the first and second plurality of cleaning elements 210 and 220 of the first example embodiment in a top view. The first cleaning elements 210 are arranged so that their bases essentially lie on a first oval around the rotation axis (which means that the vertices of the first star-shaped polygon lie on the first oval). This shall not exclude that the bases of the first cleaning elements may lie on the vertices of a first star-shaped polygon that approximates an oval, where some bases may slightly lie outside of the oval and other bases slightly lie inside of the oval. Generally and applicable to all possible embodiments, the radial distance of the vertices of the first star-shaped polygon to the rotation axis may in particular differ from the respective radial distance of a smooth curve (e.g. a portion of a helix line), in particular of a differentiable and convex closed curve such as a circle, an oval or an ellipse that approximates the first polygon and that is arranged essentially symmetrically around the rotation axis by 10% or less, optionally by 5% or less, and further optionally by 2% or less. In some embodiments, the vertices of the first star-shaped polygon may lie within a band around the rotation axis, where the radial width of the radial band may be 25% or less of the radial distance between the point where the rotation axis crosses the mounting surface and the respective center of the band. In some embodiments, the radial width may be 20% or less, 15% or less, 10% or less, 5% or less, 3% or less, 2% or less, 1% or less. The band may in particular be a circular ring (annulus), an elliptical ring, or an oval ring.

The second cleaning elements 220 are here arranged so that their bases essentially lie on a second oval around the rotation axis 203. This shall not exclude that the bases of the second cleaning elements lie on the vertices of a second star-shaped polygon that approximates an oval, where some bases may slightly lie outside of the oval and other bases may slightly lie inside of the oval. Generally and applicable to all possible embodiments, the radial distance of the vertices of the second polygon to the rotation axis may in particular differ from the respective radial distance of a differentiable and convex curve such as a circle, an oval or an ellipse that approximates the second polygon and that is arranged essentially symmetrically around the rotation axis by 10% or less, optionally by 5% or less, and further optionally by 2% or less. In some embodiments, the vertices of the second star-shaped polygon may lie within a band around the rotation axis as was discussed above with respect to the first star-shaped polygon.

In the first example embodiment, the second oval is essentially concentric with the first oval and lies inside of the first oval. In another embodiment, the first oval lies inside of the second oval. Generally and applicable to all possible embodiments having first and second cleaning elements arranged on star-shaped polygons, the first star-shaped polygon may lie either inside or outside of the second star-shaped polygon. The first and second cleaning elements 210 and 220 may be inclined with a dominant circumferential inclination portion and with none or only a slight radial inclination portion. Generally and applicable to all possible embodiments, the circumferential inclination may dominate over the radial inclination such that $r_\phi^\perp$ is larger than $r_r^\perp$, optionally wherein the ratio between $r_\phi^\perp$ and $r_r^\perp$ is larger than 2, larger than 3, larger than 4 larger than 5, larger than 10, or larger than 20. The first cleaning elements 210 may be counter-clockwise inclined and the second cleaning elements 220 may be clockwise inclined. Generally and applicable to all possible embodiments, the first cleaning elements may be all inclined either in clockwise direction or in counterclockwise direction, optionally with a dominant circumferential inclination portion. The second cleaning elements may have an circumferential inclination direction that is opposed to the circumferential inclination direction of the first cleaning elements. E.g. if all first cleaning elements are circumferentially inclined in clockwise direction, then all second cleaning elements may be circumferentially inclined in counter-clockwise direction and vice versa.

FIG. 4C shows a top view onto the first carrier 201 without mounted cleaning elements so that mounting holes 211, 221, 231 of the first, second, and third cleaning elements are visible. The geometry of the mounting holes essentially defines the cross-sectional shape, the cross-sectional area and orientation of cleaning elements realized as bristle tufts. The mounting holes 211 of the first cleaning elements comprise mounting holes 2111 of the first sub-group of first cleaning elements and mounting holes 2112 of the second sub-group of first cleaning elements that are alternately arranged. The mounting holes 2111 of the first sub-group of first cleaning elements are elongated and essentially rectangular. The long axis of the top shape of these mounting holes 2111 is oriented such that it crosses the rotation axis. In other embodiments, the long axis of the top shape of a mounting hole 2111 may be oriented such that a radial beam from the rotation axis going through the center of the mounting hole 2111 crosses the long axis at an acute angle that may be 10 degrees or less, optionally 5 degrees or less. Here, the area of the top shape of each of the mounting holes 211 of the first cleaning elements is essentially identical. In case that the first cleaning elements are realized as bristle tufts, each of the mounting holes 211 would thus accommodate an essentially identical number of individual bristles, which tends to render the manufacturing easier than in case of varying numbers of bristles per mounting hole. Alternatively, different numbers of bristles may be provided within different mounting holes. This alternative may depend or not depend on different filament calipers or filament structures/shapes that are used. The mounting holes 221 of the second cleaning elements may be similar in cross section and orientation to the mounting holes 2112 of the second sub-group of first cleaning elements. Both mounting holes 2112 and 221 may be essentially rectangular in cross section and may be only slightly elongated with the somewhat longer axis being essentially perpendicularly oriented with respect to a radial beam originating at the point where the rotation axis crosses the mounting surface and going through the centre of the mounting hole opening. The mounting holes 231 of the third cleaning elements are formed as roughly kidney-shaped holes that are each realized as a double-hole with a separation wall between the sub-holes. Each sub-hole is arranged to accommodate a single bristle tuft, but because of the proximity of the two sub-holes, the two bristle tufts will give the impression of a single, roughly kidney-shaped bristle tuft.

Generally and applicable to all embodiments, the cleaning elements may not necessarily be mounted in individual mounting holes. In some embodiments, at least two cleaning elements may be mounted in a single hole that may be elongated in the circumferential direction, where the single (elongated) hole may have separation walls, even though in some embodiments no separation walls may be present, e.g. when an anchor-free mounting technology is used. In other embodiments, at least some of the cleaning elements are arranged and then the first carrier is injection-molded around the cleaning elements. In such embodiments, a gap between adjoining cleaning elements may be essentially zero, i.e. two or more cleaning elements may then form a compact structure. In some embodiments, the cleaning elements are secured to the mounting surface, e.g. by gluing or adhering (e.g. by injection molding a TPE onto the mounting surface, which TPE enters into a material bond with the material of the first carrier).

FIG. 4D is a side view onto the cleaning head 200 of the first example embodiment. It can be seen that the first cleaning elements 210 are all inclined against the rotation axis 203 with a first inclination angle 219 in a first circumferential direction and the second cleaning elements 220 are all inclined against the rotation axis 203 with a second inclination angle 229 in a second circumferential direction opposite to the first circumferential direction. It can also be understood from this view that the first and the second cleaning elements 210 and 220 are arranged such that each first or second cleaning element is at least "crossed" by one or even more of the other cleaning elements, i.e. each first cleaning element is crossed by at least one or more second cleaning elements when viewed from the side. In other words, "crossed" means that a radial beam originating at the rotation axis 203 and being parallel to the mounting surface 202, which radial beam moves along the longitudinal centre line of a second cleaning element crosses the longitudinal centre line of at least one first cleaning element. It can be further seen that the first cleaning elements 210 have alternating length and thus have alternating heights h1 and h2. The cleaning elements of the first sub-group of first cleaning elements 2101 have a height h1 and are cut flat at their free end, the flat cut being parallel to the mounting surface 202. The cleaning elements of the second sub-group of first cleaning elements 2102 have a height h2 and are cut flat at their free end, the flat cut being parallel to the mounting surface 202.

Generally and applicable to all possible embodiments, the length of a cleaning element may be chosen to lie in a range of between about 6.0 mm and about 10.0 mm, optionally the range may be chosen to lie between about 7.0 mm and 8.5 mm. In case that the cleaning elements are realized as bristle tufts, the diameter of the individual bristle (or the diameter of the smallest circle that encloses a cross-sectional cut of the bristle in case that the bristle has a non-circular cross-sectional shape) may be chosen to lie in the range of between about 100 micrometer and about 200 micrometer, optionally in a range of between about 125 micrometer and about 175 micrometer. The absolute height difference |h1−h2| of the cleaning elements of the first and the second sub-group of first cleaning elements may be chosen to lie in a range of between about 0.5 mm and about 2.0 mm, optionally the range may be chosen to lie between about 0.7 mm and about 1.5 mm. These height differences are likely to be adequate for the curvature of regular teeth such as molars and also for the treatment of mal-positioned teeth.

Second Example Embodiment

Figure 5A:
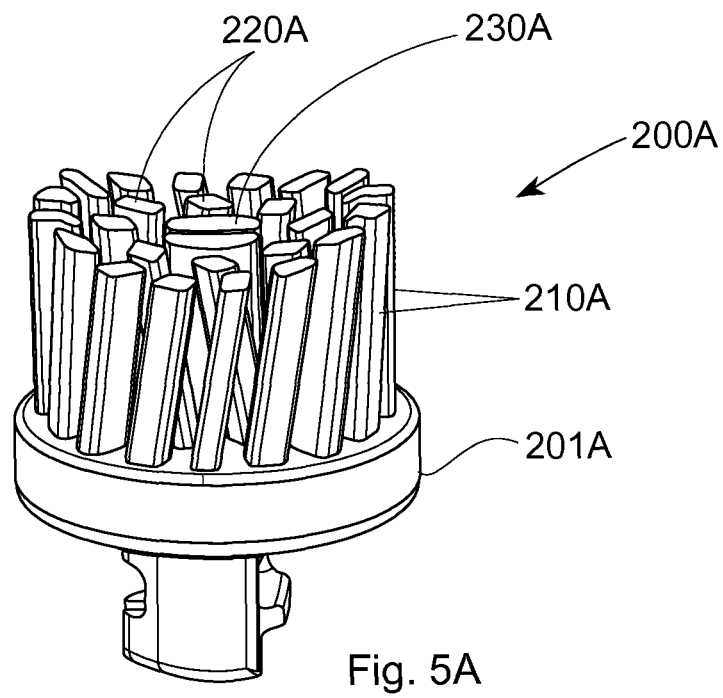
FIG. 5A is a perspective depiction of a second example embodiment of a cleaning head of a cleaning section in accordance with the present disclosure.
Figure 5B:
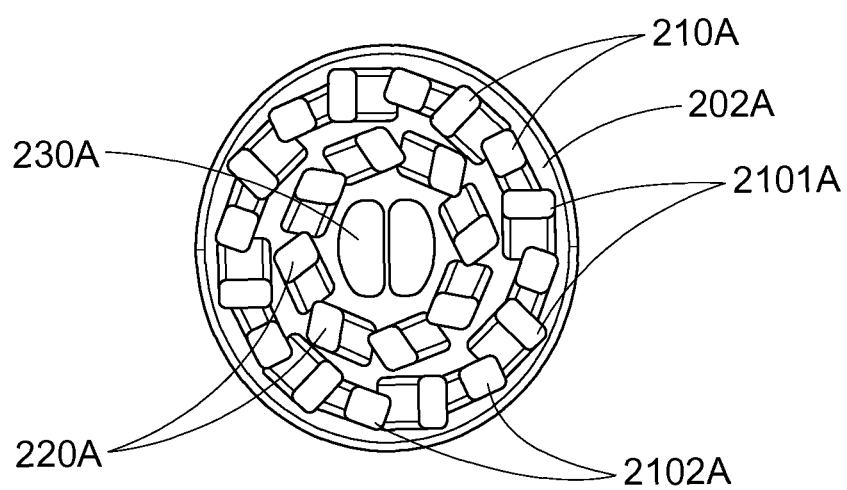
FIG. 5B is a top view onto the cleaning head shown in FIG. 5A.
Figure 5C:
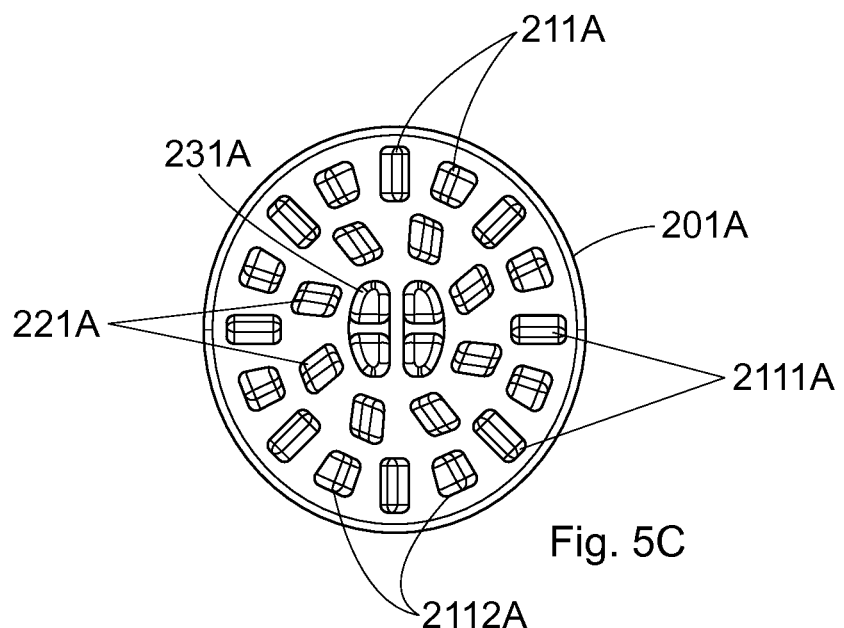
FIG. 5C is a top view onto a carrier used in the cleaning head shown in FIG. 5A without mounted cleaning elements.
Figure 5D:
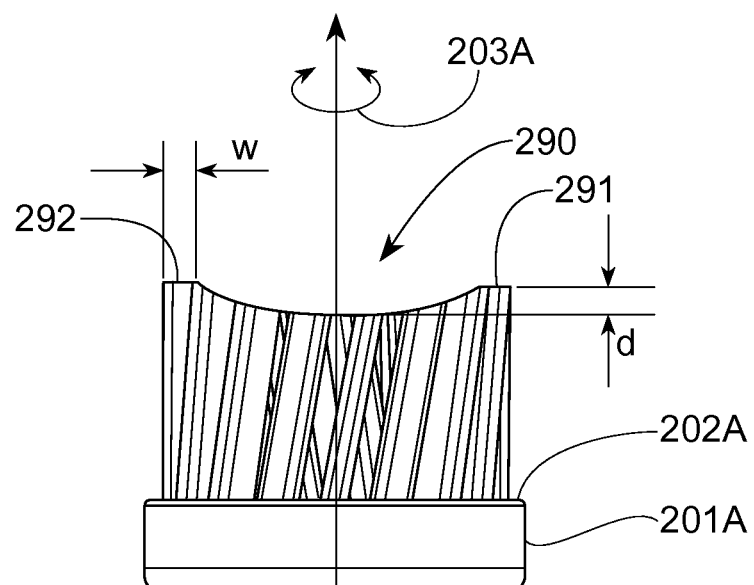
FIG. 5D is a side view onto the cleaning head shown in FIG. 5A.

FIG. 5A is a perspective view onto a second example embodiment of a cleaning head 200A in accordance with the present disclosure, FIG. 5B is a top view onto the cleaning head 200A shown in FIG. 5A, FIG. 5C is a top view onto the carrier 201A of the cleaning head 200A shown in FIG. 5A, and FIG. 5D is a side view onto the cleaning head 200A shown in FIG. 5A.

Similarly to the first example embodiment, the cleaning head 200A of the second example embodiment has first cleaning elements 210A that are circumferentially inclined in a first circumferential direction (here: in counterclockwise direction) and where cleaning elements of a first sub-group of first cleaning elements 2101A and of a second sub-group of first cleaning elements 2102A are alternately arranged. The bases of the first cleaning elements 201A are arranged on the vertices of a first star-shaped polygon around the rotation axis 202B. As may be best seen in FIG. 5C, the first sub-group of first cleaning elements 2101A has an elongated cross section, where the respective mounting holes 2111A each have a long axis that is aligned with a radial beam lying in the mounting plane 202A. The cross-sectional shape of the mounting holes 2111A is essentially rectangular. The mounting holes 2112A of the second sub-group of first cleaning elements 2102A have an essentially trapezoidal cross section, where the (here symmetrical) trapezoid tapers towards the rotation axis 203A. The symmetry axis of the trapezoid is aligned with the radial beam crossing its centre point. The second cleaning elements 220A and their respective mounting holes 221A have an essentially parallelogram-like cross section. The first cleaning elements 210A have one discretely alternating cleaning element property, namely alternating cross-sectional shape, where the shape of the cross section alternates between a first configuration (elongated, essentially rectangular shape with rounded corners) and a second configuration (trapezoidal shape with rounded corners). The first, second and third cleaning elements 210A, 220A and 230A have their free ends cut so that the free ends form an essentially oval depression 290 in the cleaning element field with two opposite flat portions 291, 292 of the cleaning element field that are parallel to the mounting surface 202A. The two flat portions 291 and 292 may each in particular be arranged to centrically lie on the longitudinal extension axis of the cleaning section such that in case the cleaning section is placed in the oral cavity the oval depression 290 can accommodate a typical tooth such as a molar and the flat portions may then enter into the interproximal areas. The maximum width w of the flat portions 291 and 292 measured along the direction of an axis connecting the centers of the opposite flat portions may be chosen to lie in a range of between about 0.75 mm and 2.0 mm, optionally this range may be chosen to lie between about 1.0 mm and 1.5 mm. These width values are likely to be physiologically adapted to the size of the interproximal areas. The depth d of the depression may lie in a range of between about 0.1 mm to about 3.0 mm, optionally in a range of between about 0.7 mm to about 2.0 mm and further optionally in a range of between about 1.0 mm to about 1.5 mm.

Third Example Embodiment

Figure 6A:
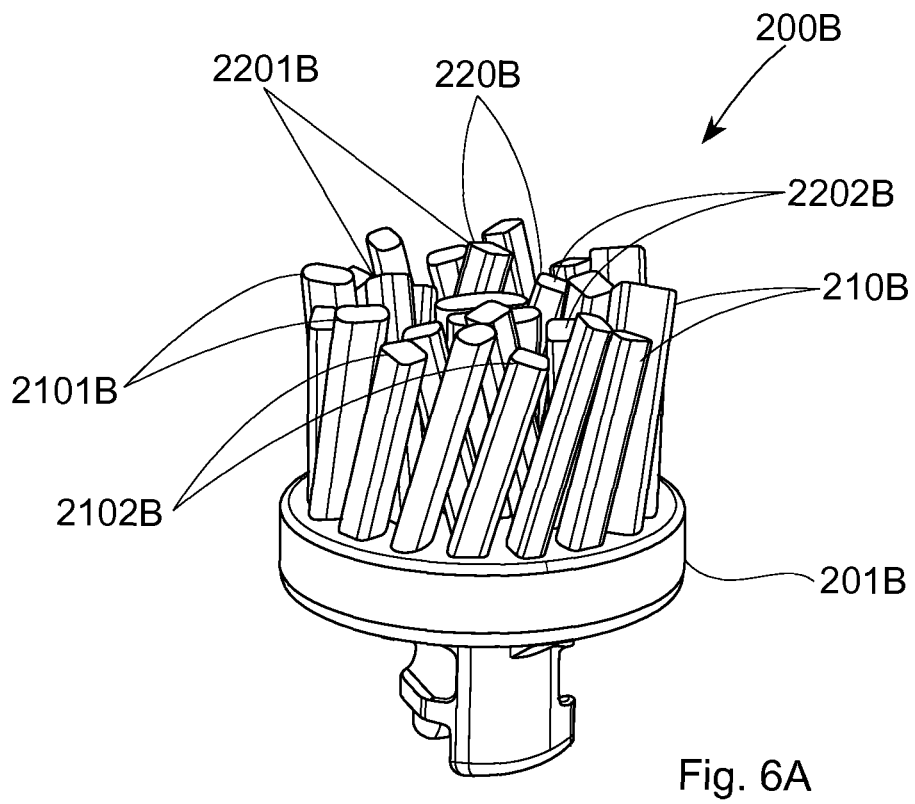
FIG. 6A is a perspective depiction of a third example embodiment of a cleaning head of a cleaning section in accordance with the present disclosure.
Figure 6B:
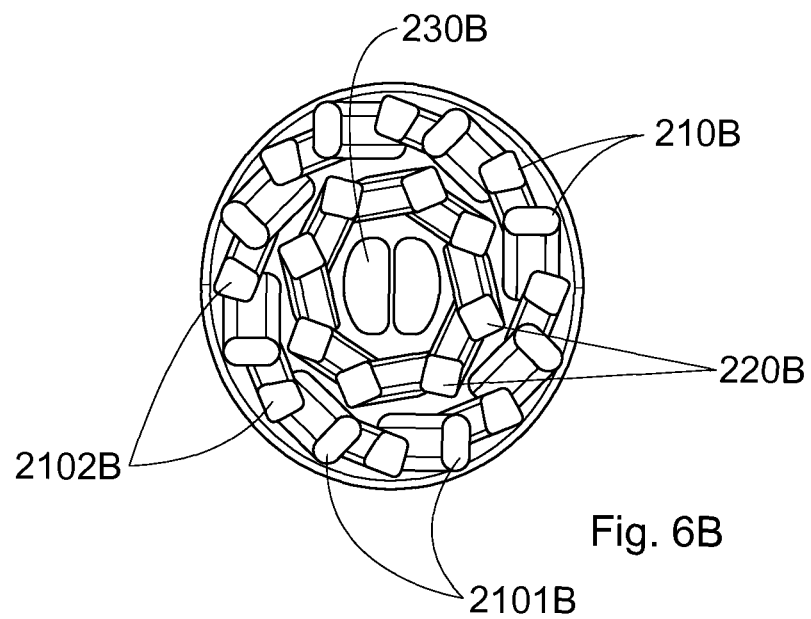
FIG. 6B is a top view onto the cleaning head shown in FIG. 6A.
Figure 6C:
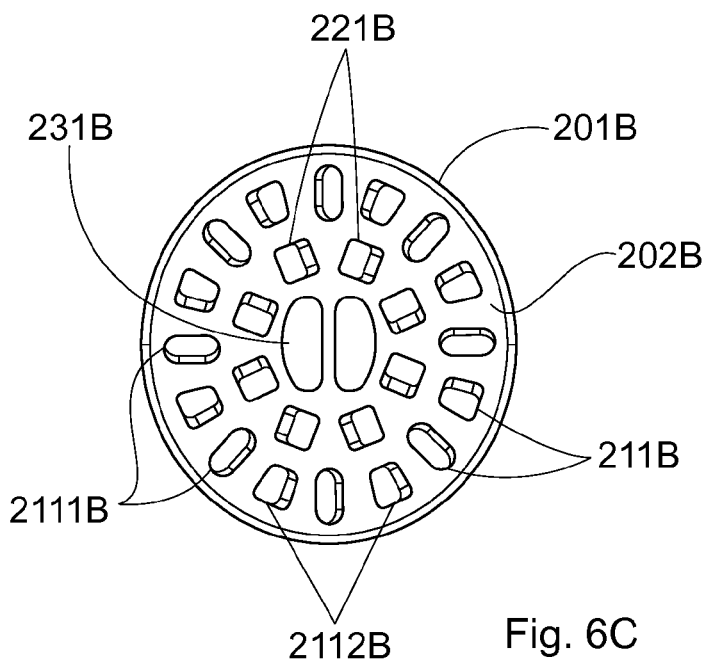
FIG. 6C is a top view onto a carrier used in the cleaning head shown in FIG. 6A without mounted cleaning elements.
Figure 6D:
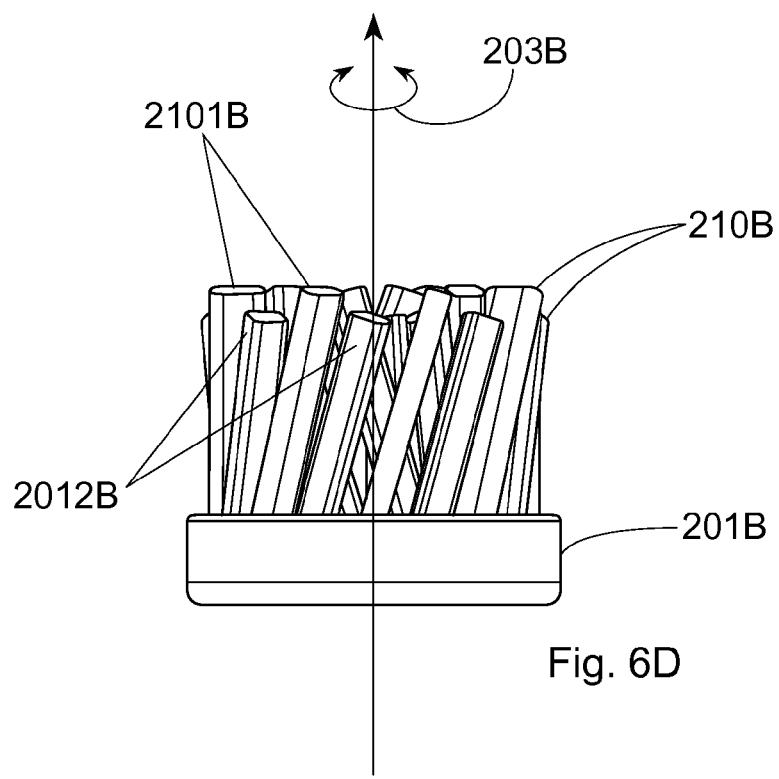
FIG. 6D is a side view onto the cleaning head shown in FIG. 6A.

FIG. 6A is a perspective view onto a third example embodiment of a cleaning head 200B in accordance with the present disclosure, FIG. 6B is a top view onto the cleaning head 200B shown in FIG. 6A, FIG. 6C is a top view onto the carrier 201B of the cleaning head 200B shown in FIG. 6A, and FIG. 6D is a side view onto the cleaning head 200B shown in FIG. 6A.

Similarly to the first example embodiment, the cleaning head 200B of the third example embodiment has first cleaning elements 210B that are all circumferentially inclined in a first circumferential direction (here: in counterclockwise direction) and where cleaning elements of a first sub-group of first cleaning elements 2101B and of a second sub-group of first cleaning elements 2102B are alternately arranged. The bases of the first cleaning elements 210B are arranged on the vertices of a first star-shaped polygon around the rotation axis 203B. As may be best seen in FIG. 6C, the cleaning elements of the first sub-group of first cleaning elements 2101B have an elongated cross section, where the mounting holes 2111B each have a long axis that is aligned with a radial beam lying in the mounting plane 202B. The cross section is in the form of a rectangle that is concluded at the small sides by semicircles. The mounting holes 2112B of the second sub-group of first cleaning elements 2102B have an essentially trapezoidal cross section, where the (here symmetrical) trapezoid tapers towards the rotation axis 203B. The symmetry axis of the trapezoid is aligned with the radial beam crossing its centre point. The second cleaning elements and their mounting holes 221B have an essentially square cross section. The first cleaning elements 210B have discretely alternating cleaning element properties, namely discretely alternating cross-sectional shape and discretely alternating height. The first and second cleaning elements 210B and 220B have flat cut free ends, where the flat cut is perpendicular to the longitudinal axis of each of the first or second cleaning elements 210B, 220B. In this second example embodiment, also the second cleaning elements 220B comprise two sub-groups 2201B and 2202B that are alternately arranged and that have discretely alternating cleaning element properties, here at least discretely alternating cleaning element height, where the height discretely alternates between two configurations, namely a first height value and a second height value.

It is again to be noted, that the herein described cross-sectional shapes of cleaning elements such as trapezoidal, parallelogram-like, elongated, rectangular, rounded rectangles etc. may be combined rather freely as long as this is not contradictory to the gist and scope of the present disclosure. E.g. parallelogram-like mounting holes may have benefits in the manufacturing of the first carrier in a plastic injection molding process, as the respective pins defining the mounting holes can be oriented such that they less likely get in conflict with pins defining other mounting holes when the pins are retracted from the mold, while the density of the mounting holes can be kept high.

Generally, the outer cleaning elements, in particular in case those are first cleaning elements, may be chosen to have a plain surface, i.e. unstructured or texture-free surface. In case the outer cleaning elements are realized as bristle tufts, the individual bristles of the outer bristles tufts may be chosen to have a plain surface. This shall not exclude that in an embodiment in which an discretely alternate cleaning element property is given by a discretely alternating bristle composition that this discretely alternate cleaning element property may be achieved by bristles having a plain surface as a first configuration of this cleaning element property and bristles having a structured surface (such as crimpled or dimpled bristles or bristles with a star-shaped or flower-shaped cross-sectional shape) as a second configuration of this cleaning element property.

Fourth Example Embodiment

Figure 7A:
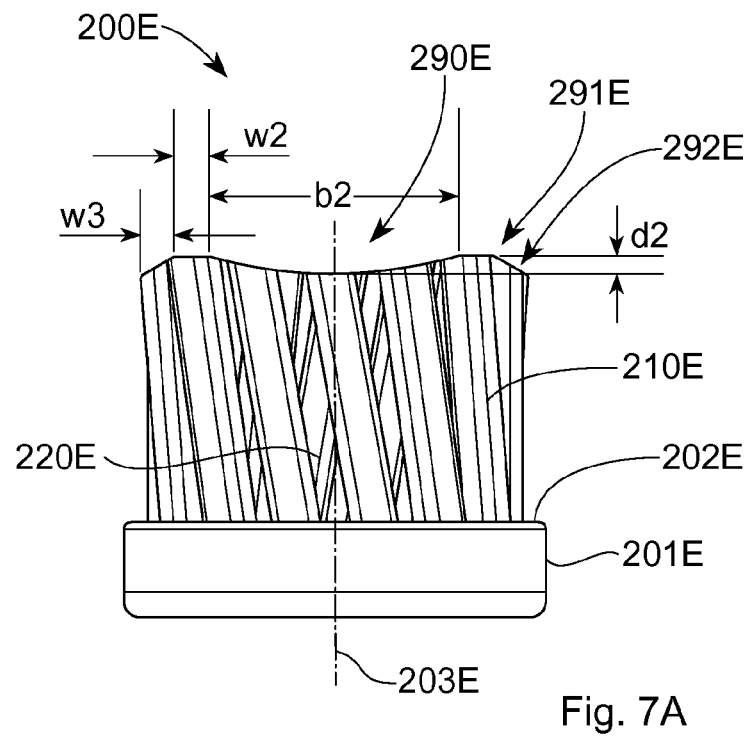
FIG. 7A is a side view onto a fourth example embodiment of a cleaning head of a cleaning section in accordance with at least one aspect of the present disclosure.
Figure 7B:
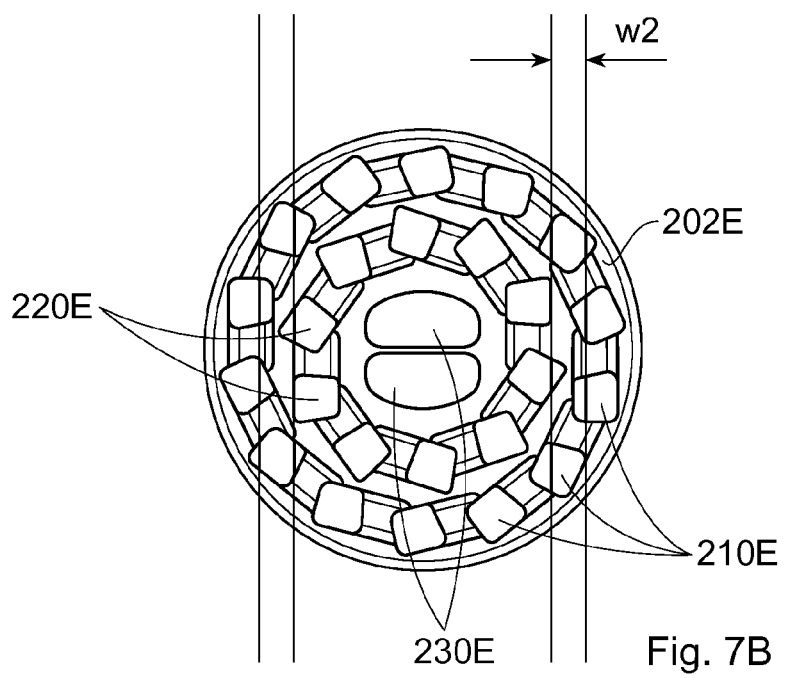
FIG. 7B is a top view onto the cleaning head shown in FIG. 7A.
Figure 7C:
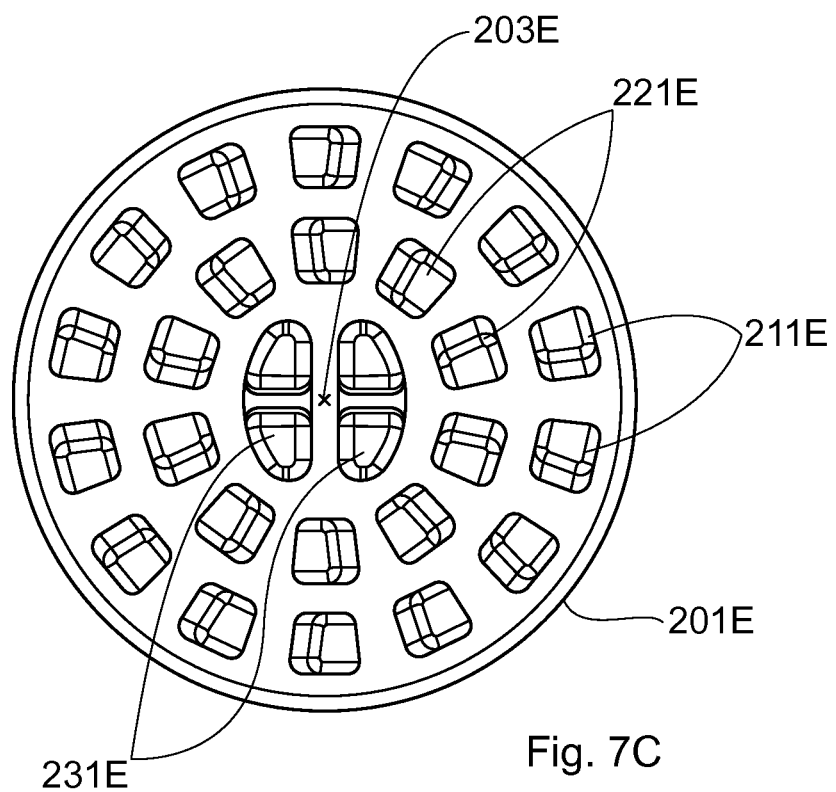
FIG. 7C is a top view onto a carrier used in the cleaning head shown in FIG. 7A without mounted cleaning elements.

FIG. 7A is a side view onto a fourth example embodiment of a cleaning head 200E in accordance with the present disclosure, FIG. 7B is a top view onto the cleaning head 200E shown in FIG. 7A, and FIG. 7C is a top view onto the carrier 201E of the cleaning head 200E shown in FIG. 7A.

The cleaning head 200E has first cleaning elements 210E and second cleaning elements 220E that are mounted on a first carrier 201E in essentially two concentric rings, where the bases of the first cleaning elements 210E are located on the vertices of a first star-shaped polygon that approximates the outer edge of a first circle and the bases of the second cleaning elements lie on the vertices of a second polygon that approximates the outer edge of a second circle. Further, third cleaning elements 230E are mounted in the centre of the first carrier 201E, where the first carrier 201E is essentially circularly shaped when viewed from the top. Here, the outer ring of first cleaning elements 210E is circumferentially inclined in clockwise direction while the second cleaning elements 220E are inclined in counterclockwise direction. The first, second and third cleaning elements 210E, 220E, 230E are cut such that the free ends of the first, second and third cleaning elements form an essentially cylindrical depression 290E, which cylindrical depression concludes in two oppositely lying flat areas 291E that are in turn each concluded by a chamfered edge 292E. The width of the circumferential depression is b2, the width of the flat portions is w2 and the width of the chamfered edges is w3, where the widths are measured in a direction perpendicular to the longitudinal axis of the cylindrical depression 290E. The depth d2 of the depression may lie in a range of between about 0.1 mm to about 3.0 mm, optionally in a range of between about 0.7 mm to about 2.0 mm and further optionally in a range of between about 1.0 mm to about 1.5 mm.

The first cleaning elements 210E all have a trapezoidal cross section. The trapezoid tapers towards the rotation axis 203E when the cross section is taken at the level of the mounting surface 202E. Form and cross sectional are of the trapezoid is here identical for the first cleaning elements as can also be seen from the mounting holes 211E. In the shown embodiment, 14 first cleaning elements 210E are mounted on the first carrier 201E. Similarly, the second cleaning elements 220E also have a trapezoidal cross section, but the trapezoid is a bit more elongated in the radial direction and less wide in circumferential direction. The cross sectional area of the cross sections of the first and second cleaning elements 210E and 220E is here chosen to be essentially identical.

The discretely alternating cleaning element property of the first cleaning elements may be realized by a discretely alternating cleaning element composition as has been discussed above. E.g. the cleaning element composition may discretely alternate between a first configuration (e.g. bristle filaments having a diameter of 100 micrometers) and a second configuration (e.g. bristle filaments having a diameter of 200 micrometers).

Fifth Example Embodiment

Figure 8:
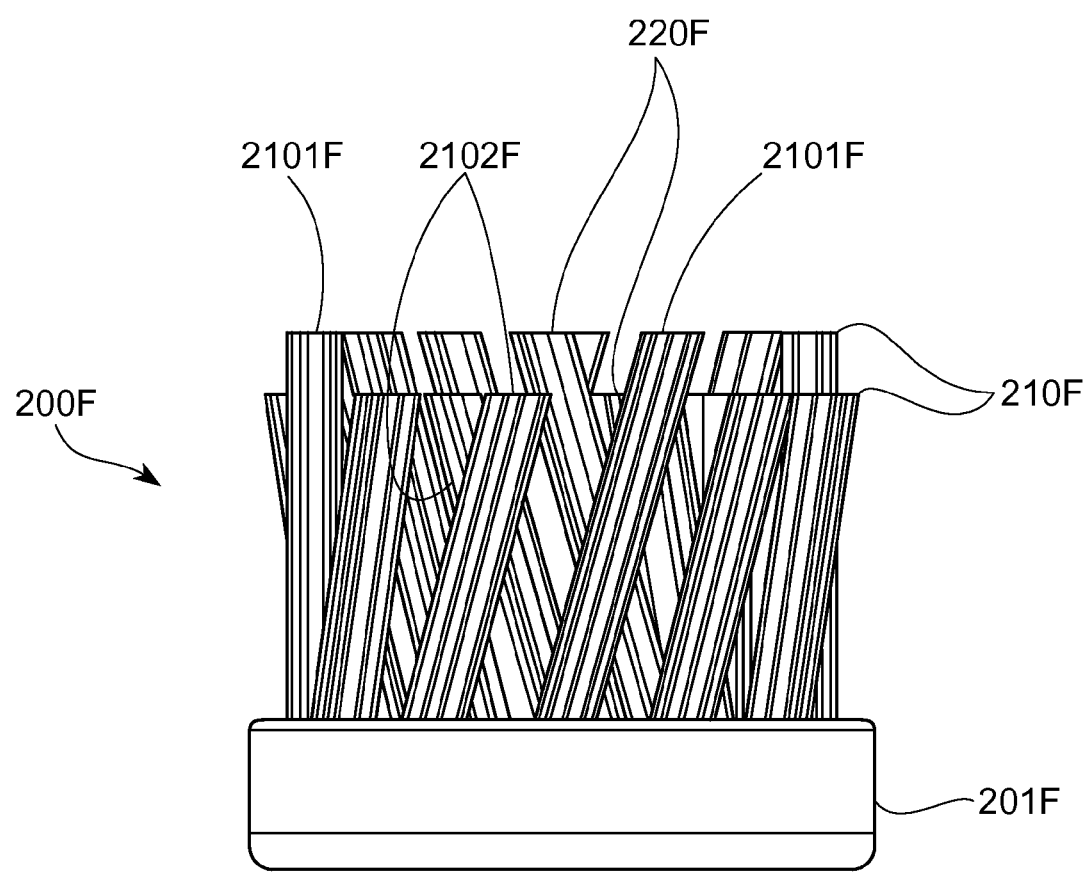
FIG. 8 is a side view onto a cleaning head having in accordance with a fifth example embodiment.

FIG. 8 shows a side view onto a cleaning head 200F in accordance with a fifth example embodiment. While the general arrangement of first and second cleaning elements 210F and 220F may be identical or similar to the previously discussed embodiments, the fifth example embodiment differs in one aspect, namely in that a cleaning element property (e.g. here: the height) does not alternate between adjacent first cleaning elements but between clusters of first cleaning elements. It is to be noted that the cleaning element property can be any of the previously described parameters. The first clusters of first cleaning elements each comprise one long cleaning element 2101F and the second clusters of first cleaning elements each comprise two short cleaning elements 2102F. That means that the discretely alternating cleaning element property is the cleaning element height. Generally speaking, if A indicates a first cleaning element having a first configuration of the discretely alternating cleaning element property and B indicates a first cleaning element having a second configuration of the discretely alternating cleaning element property different to the first configuration, then the first cleaning elements 210F are arranged as ABBABBABBAB-BABB. In the previous example embodiments, the first cleaning elements were arranged as ABABABABABABABAB. If the first cluster of the first cleaning element 2101F having the cleaning element property in its first configuration is indicated by C=A and the second cluster of first cleaning elements 2102F having the cleaning element property in its second configuration is indicated by D=BB, than the first cleaning elements 210F are arranged as CDCDCDCDCD. A first cluster C' may in another embodiment comprise also two first cleaning elements, C'=A'A', that have a cleaning element property in its first configuration, hence the arrangement would be A'A'BBA'A'BBA'A'BBA'A'BB or C'DC'DC'DC'D.

In order to alternate, each cluster of cleaning elements is at least twice available in the arrangement of first cleaning elements, e.g. CDCD, which may represent ABAB or AABAAB or ABBABB or AABBAABB etc. What was explained here for the arrangement of first cleaning elements also holds in some embodiments for the arrangement of second cleaning elements.

Further Aspects of a Cleaning Section as Proposed

In the following, a description of a particular mounting hole geometry is presented, which can be seen as an particular aspect of inclined tufts as such, i.e. it can be seen as an independent aspect of a cleaning section as such without reference to the other aspect discussed in the present application. But as it relates to inclined tufts, it may additionally be seen as a further aspect of cleaning sections as described before.

Figure 9A:
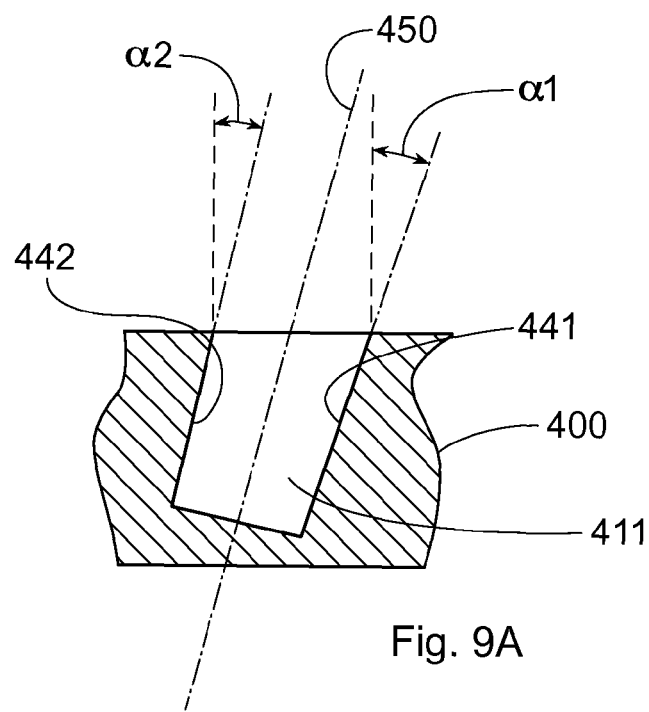
FIG. 9A is a cross sectional cut through a first example tufting hole.

FIG. 9A is a schematic cross sectional cut through a first carrier 400 with a first example embodiment of a mounting hole 411 present in the first carrier 400 that can be utilized for anchor tufting of a cleaning element realized as a bristle tuft. The cross sectional cut of the mounting hole 411 may be taken in circumferential direction through a tuft hole as shown in FIG. 4C or FIG. 5C or FIG. 6C or FIG. 7C. The dashed-dotted line 450 indicates the central line of the cleaning element to be mounted into the mounting hole 411. The dashed-dotted line 450 coincides with the circumferential inclination of the cleaning element to be mounted. The "inner", first circumferential wall 441 of the tuft hole 411, i.e. the wall against which the cleaning will rest in its mounted state, is inclined against a normal on the mounting surface with an inclination angle of $\alpha 1$. The opposite, second wall 442 is inclined against a normal on the mounting surface with an inclination angle of $\alpha 2$, where $\alpha 1 > \alpha 2$. Thus, the tufting hole 411 has an essentially trapezoidal cross section in this vertical cross-sectional cut. The absolute value of the difference in the inclination angles $\alpha 2$ and $\alpha 1$ may be chosen to lie in a range of between about 0.1 degrees to about 4.0 degrees.

Figure 9B:
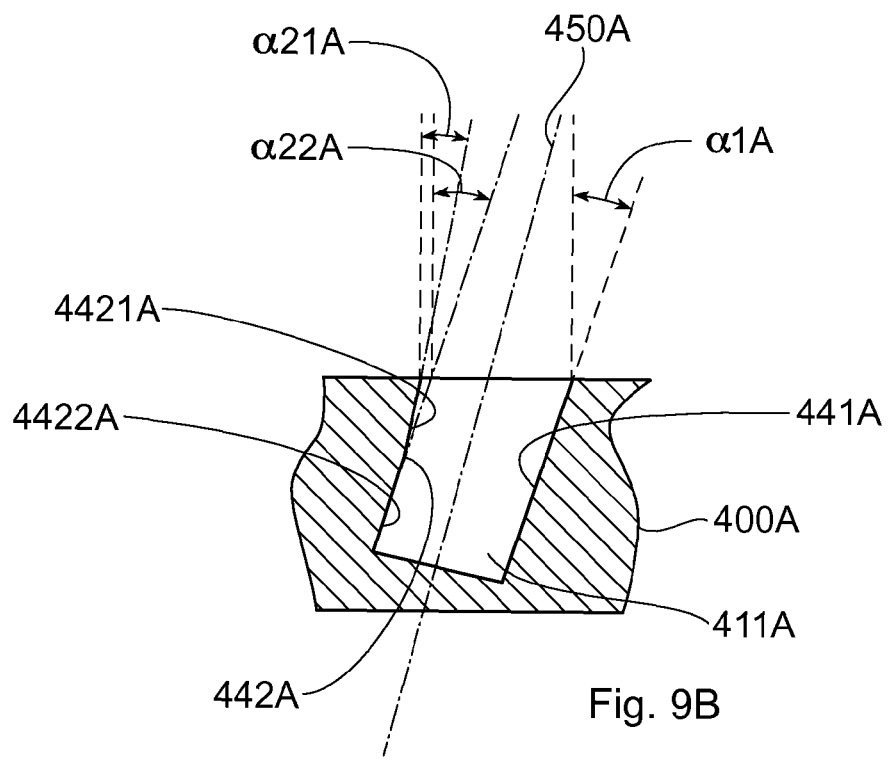
FIG. 9B is a cross sectional cut through a second example tufting hole.

FIG. 9B is a schematic cross sectional cut through a carrier 400A with a second example embodiment of a mounting hole 411A present in the carrier that can be utilized for anchor tufting of a cleaning element realized as a bristle tuft. In this second example embodiment, the outer wall 442A of the tufting hole 411A has a lower wall section 4422A that is inclined with an angle $\alpha 22A$ that is similar or identical to the inclination angle $\alpha 1A$ of the inner wall 441A. The outer wall 442A has a second upper wall section 4421A that is inclined with an angle $\alpha 21A$ that is smaller than the inclination angle $\alpha 1A$ of the inner wall 441A. The absolute value of the difference in the inclination angles α21A and α1A may be chosen to lie in a range of between about 0.1 degrees to about 4.0 degrees.

Alternately or additionally, the other walls of a tufting hole, i.e. the walls defining the tufting hole essentially in radial direction, may likewise be differently inclined, where the inclination angle of each radial wall may be chosen to lie in a range of between about 0 degrees to about ±4 degrees.

Without loss of generalization, the tuft holes described with reference to FIGS. 9A and 9B may in some embodiments not have a lower bottom as is indicated in FIGS. 9A and 9B, but the tuft holes may be through holes provided in a first carrier.

Thus, a cleaning section is described, wherein at least one cleaning element is mounted in a mounting hole provided in a first carrier, which mounting hole has at least two opposite side walls that diverge over at least a length portion proximal to a mounting surface of the first carrier, optionally wherein the angular difference in the wall inclinations lies in a range of between about 0.1 degree and about 10 degrees or more preferably between 0.1 degree and about 4.0 degrees. In some embodiments, the mounting hole is arranged as a through hole, and in other embodiments, the mounting holes have a lower bottom. In some embodiments, a plurality of mounting holes as described may be present on the first carrier and optionally at least two of the plurality of mounting holes may have different inclination angle values for α1, α2 or α21A, wherein further optionally, each mounting hole may have any of the designs shown in FIGS. 9A and 9B.

The mounting surface and thus the diameter of the first carrier may be chosen to lie in a range of between about 7 mm to about 18 mm, optionally between about 8 mm to about 15 mm. The first carrier may be oval or ellipsoidal instead of circular, were the longer axis may be chosen to lie in a range of between about 11 mm to about 18 mm and the small axis may be chosen to lie in a range of between about 7 mm to about 14 mm.

In another example embodiment, the mounting surface of the first carrier may be arranged to lie in a plane that is not perpendicular to the rotation axis, i.e. the mounting surface and thus the whole cleaning element arrangement may be arranged with an additional offset angle with respect to the rotation axis. In operation this will lead to an additional wobbling motion of the cleaning head and thus the cleaning properties of the cleaning section can be modified over embodiments were the mounting surface is perpendicular to the rotation axis.

Figure 10:
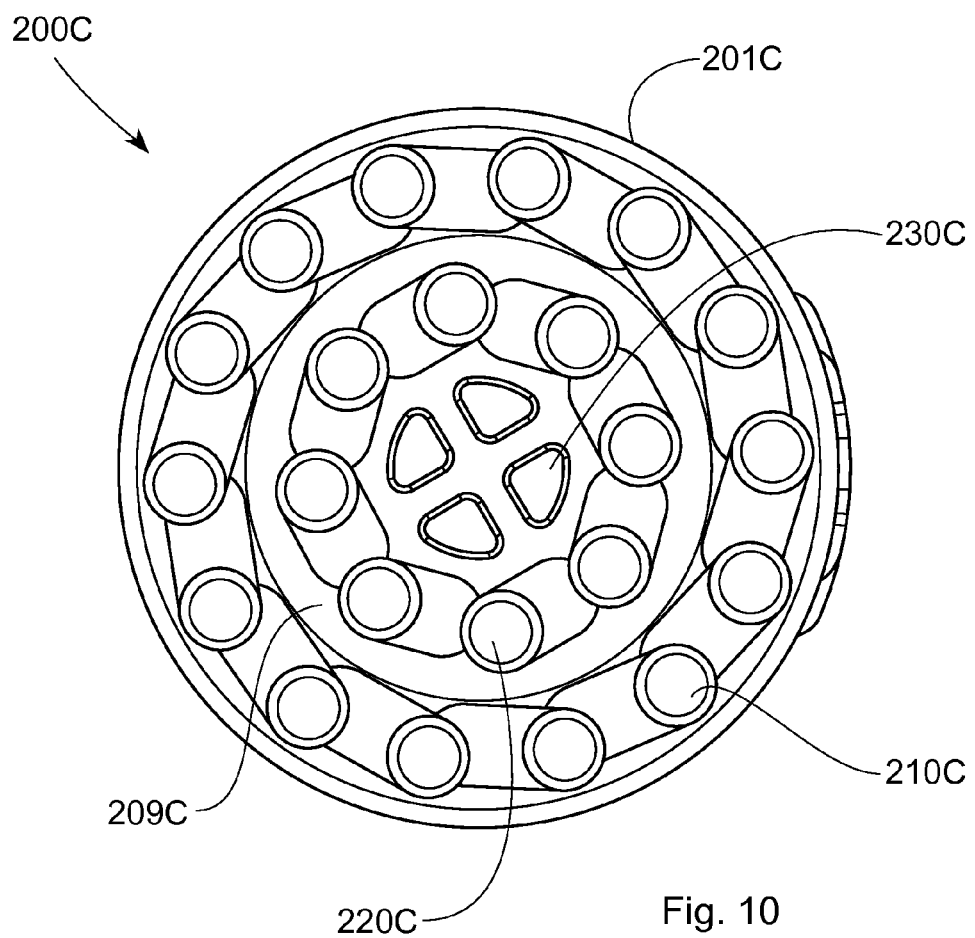
FIG. 10 is a top view onto an example cleaning head having two coaxially arranged carriers.

FIG. 10 is a top view onto a cleaning head 200C of a further example embodiment. Here, the first cleaning elements 210C are arranged on a first carrier 201C. The bases of the first cleaning elements 210C are arranged on the vertices of a first star-shaped polygon around the rotation axis. The first cleaning elements 210C are all inclined in a first circumferential direction (here: in counterclockwise direction). The second cleaning elements 220C are arranged on a second carrier 209C. The second carrier 209C is coaxially arranged with the first carrier 201C. The second carrier may be arranged to be static, i.e. the second carrier will not be driven during operation, or the second carrier may be arranged to be driven in counter direction or with phase difference relative to the first carrier during operation. Further third cleaning elements 230C are mounted on the second carrier 209C. The cleaning properties of a cleaning head as shown are likely to improve over or to be at least different to embodiments with only a single carrier as the first and second cleaning elements can perform different motions.

Figure 11:
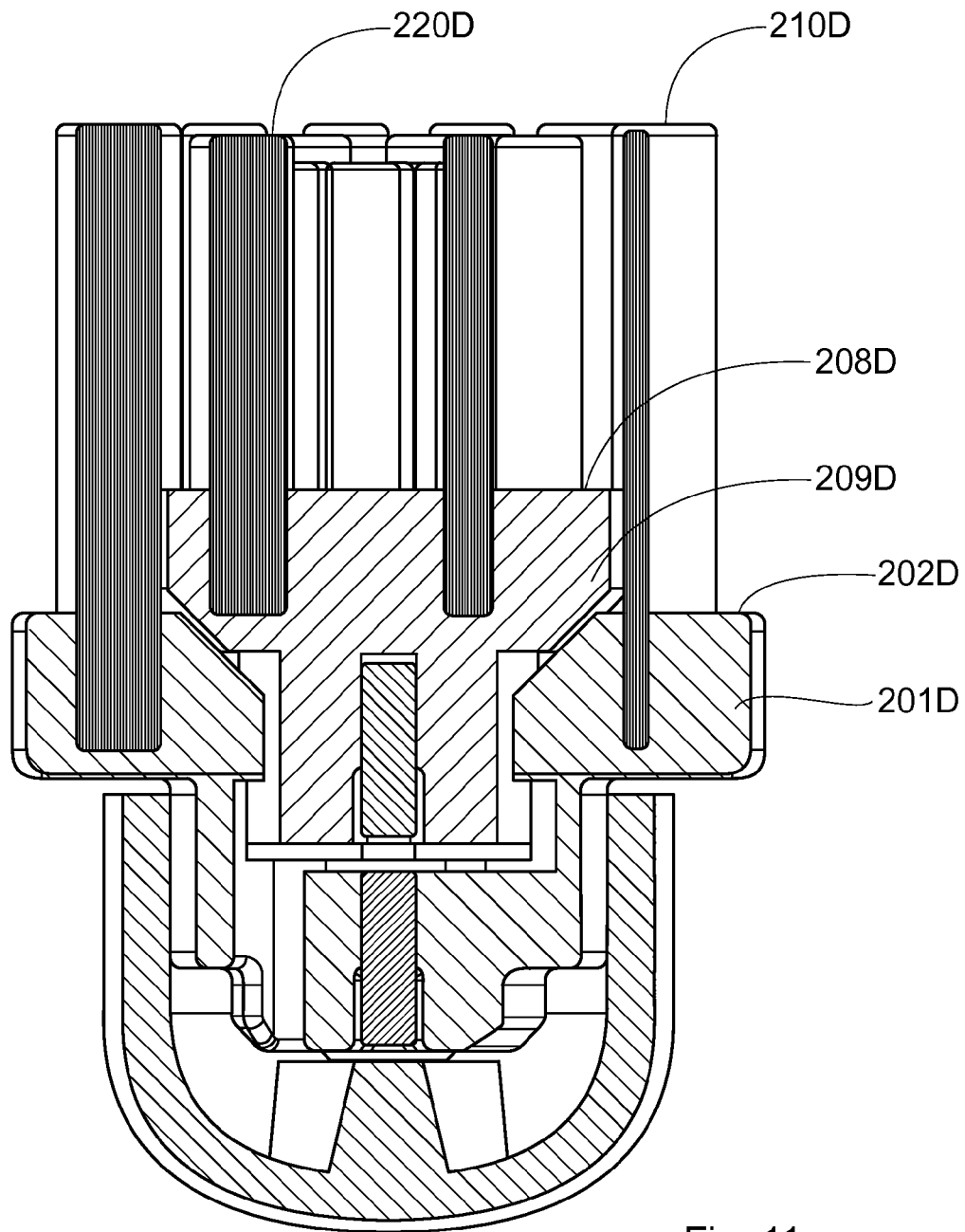
FIG. 11 is a cross sectional cut through a further example cleaning section where the cut plane goes through a cleaning head comprising two coaxially arranged carriers.

FIG. 11 is a cross sectional cut through an example cleaning section in which the cleaning head 200D comprises a first carrier 201D and a second carrier 209D that are coaxially arranged. It can be seen that the mounting surface 208D of the second carrier 209D lies above the mounting surface 202D of the first carrier and that the first carrier 201D extends underneath the second carrier 209D. In such an arrangement, the first and second cleaning elements 210D and 220D can be as close together as if they were mounted on a single carrier. In the embodiment shown in FIG. 11, the cleaning elements are straight, i.e. they extend parallel to the rotation axis. This indicates that the provision of two coaxially arranged carriers of which at least one carrier is arranged for driven rotation or oscillation around the central axis (i.e. rotation axis) and were the mounting surfaces of the two carriers are arranged at different heights may be considered as an individual aspect of a cleaning section for an electric oral hygiene device independent on any other features described in the present disclosure.

In at least some of the discussed embodiments, the cross-sectional shape of the cleaning elements varied and several shapes such as (essentially) rectangular, (essentially) square, (essentially) trapezoidal, (essentially) parallelogram-like, (essentially) triangular etc. were shown. It was discussed that in accordance with one aspect, the cross sectional shape of the cleaning elements mounted in respectively shaped mounting holes may be chosen such that pins defining the mounting holes in a plastic injection molding process of the first carrier can be retracted from the mold without getting into conflict with each other. In accordance with another aspect, the cross-sectional shape may be chosen in order to achieve a high and moreover relatively homogenous density of cleaning elements on the mounting surface. A density of cleaning elements that varies by about 25% or less may be considered as desirable. Desirable densities of cleaning elements, in particular of cleaning elements realized as bristle tufts, lie at or above 30% filled area of the mounting surface of the first carrier.

In the present description, the term "cleaning element" is used to describe all cleaning elements that are present in an embodiment of a cleaning section and thus may mean any first, second or third cleaning element or any other cleaning element that may be present.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

The invention claimed is:

1. A cleaning section for an electric oral hygiene device, comprising:
   at least a first carrier mounted for driven rotation or oscillating rotation around a rotation axis; and
   at least a plurality of first cleaning elements mounted on a mounting surface of the first carrier with their bases arranged on vertices of a first star-shaped polygon around the rotation axis;
   wherein all of the first cleaning elements are circumferentially inclined in the same circumferential direction with respect to the rotation axis such that a free end of each of the first cleaning elements is farther away in the circumferential direction than the base of the respective first cleaning element;
   wherein the first cleaning elements form an outermost ring of a plurality of rings of cleaning elements;

wherein at least one first cleaning element has a first height measured between the mounting surface of the first carrier and the free end of the first cleaning element in direction of the rotation axis and at least one first cleaning element has a second height, wherein the distance between the two height values lies in a range of between about 0.1 mm and about 3.0 mm;

wherein the shape of the cross-sections of the first cleaning elements alternate between an elongate shape such as an essentially rectangular shape and a more compact shape such as an essentially square shape or an essentially trapezoidal shape;

wherein at least one cleaning element property of a length of the cleaning element and an area of a cross section of the cleaning element discretely alternates between adjacent first cleaning elements or adjacent clusters of first cleaning elements; and wherein circumferential inclination angles of at least the first cleaning elements lie in a range of between about 10 degrees to about 16 degrees;

wherein the first cleaning elements have an additional penetration amplitude in a relative range of between about 1.5% and 3.9% of the length of the cleaning element.

2. The cleaning section according to claim 1, wherein a plurality of second cleaning elements is mounted on the first carrier with their bases arranged on vertices of a second star-shaped polygon around the rotation axis, wherein the bases lie on a mounting surface and the whole interior of the second star-shaped polygon is visible from a point where the rotation axis crosses the mounting surface, the second star-shaped polygon being disposed inside of the first star-shaped polygon, wherein all of the second cleaning elements are circumferentially inclined in a circumferential direction that is opposite to the circumferential direction in which all the first cleaning elements are inclined.

3. The cleaning section according to claim 1, wherein a location and/or the cross-sectional shapes of the cleaning elements mounted on the first carrier is chosen such that a ratio between an area filled by cleaning elements and an area not filled with cleaning elements varies by about 25% or less.

4. The cleaning section according to claim 1, wherein at least one cleaning element is mounted in a mounting hole provided in the first carrier, which mounting hole has at least two opposite side walls that diverge over at least a length portion proximal to a mounting surface of the first carrier, wherein the angular difference in the wall inclinations lies in a range of between about 0.1 degree and about 10 degrees.

5. The cleaning section according to claim 1, wherein the bases of the first cleaning elements lie on a differentiable, not self-intersecting, convex and closed curve around the rotation axis such as the edge of a circle, an ellipse, or an oval, wherein the bases of the first cleaning elements lie within a radial band around the rotation axis, which radial band has a radial width that is 25% or less than the radial distance between the respective band centre and the point where the rotation axis intersects the mounting surface.

* * * * *